United States Patent
Mahmood et al.

(10) Patent No.: US 10,995,366 B2
(45) Date of Patent: *May 4, 2021

(54) METHODS AND DEVICES FOR DETECTION AND ACQUISITION OF BIOMARKERS

(71) Applicants: MINDERA CORPORATION, South San Francisco, CA (US); The Scripps Research Institute, La Jolla, CA (US)

(72) Inventors: Tahir A. Mahmood, Burlingame, CA (US); Tobin J. Dickerson, San Diego, CA (US); Nadir A. Mahmood, San Francisco, CA (US); Petr Capek, San Diego, CA (US)

(73) Assignees: MiNDERA Corporation, San Diego, CA (US); The Scripps Research Institute, Lo Jolla (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/367,015

(22) Filed: Dec. 1, 2016

(65) Prior Publication Data

US 2017/0145489 A1 May 25, 2017

Related U.S. Application Data

(63) Continuation of application No. 14/106,661, filed on Dec. 13, 2013, now Pat. No. 9,540,684.

(60) Provisional application No. 61/737,237, filed on Dec. 14, 2012.

(51) Int. Cl.

| | |
|---|---|
| *C12Q 1/6841* | (2018.01) |
| *A61K 9/00* | (2006.01) |
| *C12Q 1/6806* | (2018.01) |
| *A61B 5/15* | (2006.01) |
| *A61B 5/145* | (2006.01) |
| *A61B 5/1468* | (2006.01) |
| *A61B 10/02* | (2006.01) |
| *A61B 10/00* | (2006.01) |
| *C12Q 1/6837* | (2018.01) |
| *C12Q 1/6876* | (2018.01) |
| *G01N 1/08* | (2006.01) |
| *A61B 5/00* | (2006.01) |

(52) U.S. Cl.
CPC .......... *C12Q 1/6841* (2013.01); *A61B 5/1468* (2013.01); *A61B 5/14503* (2013.01); *A61B 5/14514* (2013.01); *A61B 5/150015* (2013.01); *A61B 5/150022* (2013.01); *A61B 5/150984* (2013.01); *A61B 10/0045* (2013.01); *A61B 10/0233* (2013.01); *A61K 9/0021* (2013.01); *C12Q 1/6806* (2013.01); *C12Q 1/6837* (2013.01); *C12Q 1/6876* (2013.01); *G01N 1/08* (2013.01); *A61B 5/685* (2013.01); *A61B 2010/008* (2013.01); *A61B 2562/046* (2013.01); *C12Q 2600/16* (2013.01)

(58) Field of Classification Search
CPC .......................... C12Q 1/6841; A61B 5/14514
USPC ............................................................ 506/9
See application file for complete search history.

(56) References Cited

U.S. PATENT DOCUMENTS

| | | | |
|---|---|---|---|
| 4,683,202 A | 7/1987 | Mullis | |
| 6,293,925 B1 | 9/2001 | Safabash et al. | |
| 6,503,231 B1 | 1/2003 | Prausnitz et al. | |
| 6,663,820 B2 | 12/2003 | Arias et al. | |
| 6,743,211 B1 | 6/2004 | Prausnitz et al. | |
| 6,749,575 B2 | 6/2004 | Matriano et al. | |
| 6,855,131 B2 | 2/2005 | Trautman et al. | |
| 6,881,203 B2 | 4/2005 | Delmore et al. | |
| 7,332,197 B2 | 2/2008 | Wood et al. | |
| 7,416,541 B2 | 8/2008 | Yuzhakov et al. | |
| 9,540,684 B2 | 1/2017 | Mahmood et al. | |
| 2002/0032415 A1 | 3/2002 | Trautman et al. | |
| 2002/0087182 A1 | 7/2002 | Trautman et al. | |
| 2002/0110828 A1* | 8/2002 | Ferea .................... | C12Q 1/6837 435/6.11 |
| 2003/0027154 A1* | 2/2003 | Narahara .............. | B01J 19/0046 435/6.12 |
| 2003/0036710 A1 | 2/2003 | Matriano et al. | |
| 2003/0211528 A1 | 11/2003 | Iscove | |
| 2004/0181203 A1 | 9/2004 | Cormier et al. | |
| 2005/0178760 A1 | 8/2005 | Chang | |
| 2007/0148654 A1* | 6/2007 | Nakagawa ........... | B01J 19/0046 435/6.11 |
| 2007/0148690 A1 | 6/2007 | Shao et al. | |

(Continued)

FOREIGN PATENT DOCUMENTS

| | | |
|---|---|---|
| AU | 2012213965 A1 | 9/2012 |
| CN | 1688693 A | 10/2005 |

(Continued)

OTHER PUBLICATIONS

Tang et al. (Nature Methods, vol. 6, No. 5, May 2009, pp. 377-382, and online methods (Year: 2009).*

(Continued)

*Primary Examiner* — Karla A Dines
(74) *Attorney, Agent, or Firm* — Wilson Sonsini Goodrich & Rosati

(57) ABSTRACT

The present invention provides devices and methods for detecting and capturing molecular biomarkers from a subject in situ. Specifically, the devices contain an array of microneedles to which are attached probes specific for one or more biomarkers of interest. The devices can be used directly on a subject (e.g., via skin piercing) in detecting the biomarkers in the body of the subject (e.g., tissues, blood stream).

38 Claims, 8 Drawing Sheets

Specification includes a Sequence Listing.

(56) References Cited

U.S. PATENT DOCUMENTS

| | | | |
|---|---|---|---|
| 2008/0039339 A1* | 2/2008 | Hassibi | C12Q 1/6818 506/9 |
| 2009/0062752 A1 | 3/2009 | Gonnelli | |
| 2010/0003189 A1 | 1/2010 | Tlsty et al. | |
| 2010/0106105 A1 | 4/2010 | Yeshurun et al. | |
| 2010/0178651 A1 | 7/2010 | Hatzis et al. | |
| 2010/0185142 A1 | 7/2010 | Kamen et al. | |
| 2010/0286290 A1* | 11/2010 | Lohmann | C12Q 1/6844 514/789 |
| 2011/0028905 A1 | 2/2011 | Takada | |
| 2011/0160069 A1 | 6/2011 | Corrie et al. | |
| 2011/0191874 A1 | 8/2011 | Carlock et al. | |
| 2011/0270221 A1 | 11/2011 | Ross | |
| 2011/0270223 A1 | 11/2011 | Sullivan et al. | |
| 2011/0288389 A9 | 11/2011 | Levinson et al. | |
| 2011/0294996 A1* | 12/2011 | Scheiber | C12Q 1/68 536/23.1 |
| 2011/0295149 A1 | 12/2011 | Mitragotri et al. | |
| 2012/0034598 A1 | 2/2012 | Holmes et al. | |
| 2012/0109613 A1 | 5/2012 | Boyden et al. | |
| 2012/0172820 A1 | 7/2012 | Cannehan et al. | |
| 2014/0287942 A1 | 9/2014 | Mahmood et al. | |

FOREIGN PATENT DOCUMENTS

| | | |
|---|---|---|
| EP | 2119469 A1 | 11/2009 |
| WO | WO-0022108 A1 | 4/2000 |
| WO | WO-0175447 A1 | 10/2001 |
| WO | WO-0212891 A1 | 2/2002 |
| WO | WO-2009140735 A1 | 11/2009 |

OTHER PUBLICATIONS

Arenkov, et al. Protein Microchips: Use for Immunoassay and Enzymatic Reactions. Analytical Biochemistry. 2000; 278(2):123-131.
Chen, et al. Analysis of GD2/GM2 synthase mRNA as a biomarker for small cell lung cancer. Lung Cancer. Feb. 2010; 67(2):216-20. doi: 10.1016/j.lungcan.2009.04.009. Epub May 19, 2009.
Day, et al. Immobilization of polynucleotides on magnetic particles. Factors influencing hybridization efficiency. Biochem J. Sep. 15, 1991;278 ( Pt 3):735-40.
Eckert, et al. DNA polymerase fidelity and the polymerase chain reaction. PCR Methods Appl. Aug. 1991;1(1):17-24.
European search report and opinion dated Jul. 27, 2016 for EP Application No. 13862428.
Fodor, et al. Light-directed, spatially addressable parallel chemical synthesis. Science. Feb. 15, 1991;251(4995):767-73.
Gonzalo, et al. Telomerase mRNA expression and immunohistochemical detection as a biomarker of malignant transformation in patients with inflammatory bowel disease. Gastroenterol Hepatol. 2010; 33(4):288-96. doi: 10.1016/j.gastrohep.2009.12.011.
Goto, et al. High molecular weight-melanoma-associated antigen as a biomarker of desmoplastic melanoma. Pigment Cell & Melanoma Research. 2010; 23:137-140.
Guatelli, et al. Isothermal, in vitro amplification of nucleic acids by a multienzyme reaction modeled after retroviral replication. Proc Natl Acad Sci U S A. Mar. 1990;87(5):1874-8.
Guo, et al. Direct fluorescence analysis of genetic polymorphisms by hybridization with oligonucleotide arrays on glass supports. Nucleic Acids Res. Dec. 11, 1994;22(24):5456-65.
Hojfeldt, et al. A cleavable amino-thiol linker for reversible linking of amines to DNA. J Org Chem. Dec. 8, 2006;71(25):9556-9.
International search report and written opinion dated May 9, 2014 for PCT/US2013/075187.
Jacobs, et al. Screening for ovarian cancer: a pilot randomised controlled trial. Lancet. 1999; 353(9160):1207-1210.
Jansen, et al. β-Defensin-2 Protein Is a Serum Biomarker for Disease Activity in Psoriasis and Reaches Biologically Relevant Concentrations in Lesional Skin. PLoS ONE. 2009; 4(3): e4725.
Johnson, et al. C-Reactive Protein as a Clinically Useful Biomarker of Metastasis of Renal Cell Carcinoma. Molecular Diagnosis & Therapy. 2010; 14(3):191-193.
Jyoung, et al. Immunosensor for the detection of Vibrio cholerae O1 using surface plasmon resonance. Biosensors and Bioelectronics. 2006; 21(12):2315-2319.
Kunz, et al. DNA microarray technology and its applications in dermatology. Exp Dermatol. Oct. 2004;13(10):593-606.
Kwoh, et al. Transcription-based amplification system and detection of amplified human immunodeficiency virus type 1 with a bead-based sandwich hybridization format. Proc Natl Acad Sci U S A. Feb. 1989;86(4):1173-7.
Lamture, et al. Direct detection of nucleic acid hybridization on the surface of a charge coupled device. Nucleic Acids Res. Jun. 11, 1994;22(11):2121-5.
Landegren, et al. A ligase-mediated gene detection technique. Science. Aug. 26, 1988;241(4869):1077-80.
Li, et al. Insulin-like growth factor II mRNA-binding protein 3: A novel prognostic biomarker for oral squamous cell carcinoma. Head Neck. 2011; 33(3):368-374.
Liu, et al. A genome-wide association study of psoriasis and psoriatic arthritis identifies new disease loci. PLoS Genet. Mar. 28, 2008;4(3):e1000041. doi: 10.1371/journal.pgen.1000041.
Lu, et al. Oriented Immobilization of Fab' Fragments on Silica Surfaces. Anal. Chem. 1995; 67(1):83-87.
Macbeath, et al. Printing Proteins as Microarrays for High-Throughput Function Determination. Science. 2000; 289:1760-1763.
Mathelin, et al. Serum biomarkers for detection of breast cancers: a prospective study. Breast Cancer Research and Treatment. 2006; 96:83-90.
Mattila, et al. Fidelity of DNA synthesis by the Thermococcus litoralis DNA polymerase—an extremely heat stable enzyme with proofreading activity. Nucleic Acids Res. Sep. 25, 1991;19(18):4967-73.
Mendoza, et al. High-Throughput Microarray-Based Enzyme-Linked Immunosorbent Assay (ELISA). BioTechniques. 1999; 27:778-788.
Miura, et al. Clinical impact of serum transforming growth factor-alpha mRNA as a predictive biomarker for the prognosis of fulminant hepatitis. Hepatol Int. Jun. 2008;2(2):213-21. doi: 10.1007/s12072-008-9053-6. Epub Apr. 9, 2008.
Miura, et al. Serum human telomerase reverse transcriptase messenger RNA as a novel tumor marker for hepatocellular carcinoma. Clin Cancer Res. May 1, 2005;11(9):3205-9.
Nakanishi, et al. A novel method of immobilizing antibodies on a quartz crystal microbalance using plasma-polymerized films for immunosensors. Anal Chem. May 15, 1996;68(10):1695-700.
Notice of Allowance dated Oct. 20, 2016 for U.S. Appl. No. 14/106,661.
Office action dated Jul. 30, 2015 for U.S. Appl. No. 14/106,661.
Office action dated Sep. 8, 2016 for U.S. Appl. No. 14/106,661.
Office action dated Dec. 22, 2015 for U.S. Appl. No. 14/106,661.
Paige, et al. RNA mimics of green fluorescent protein. Science. Jul. 29, 2011;333(6042):642-6. doi: 10.1126/science.1207339.
Polascik, et al. Prostate specific antigen: a decade of discovery—what we have learned and where we are going. Journal of Urology. 1999; 162(2):293-306.
Rowe, et al. An array immunosensor for simultaneous detection of clinical analytes. Anal Chem. Jan. 15, 1999;71(2):433-9.
Sakamoto, et al. WT1 mRNA level in peripheral blood is a sensitive biomarker for monitoring minimal residual disease in acute myeloid leukemia. Tohoku J Exp Med. Oct. 2009;219(2):169-76.
Sato, et al. Establishment of a new method, transcription-reverse transcription concerted reaction, for detection of plasma hnRNP B1 mRNA, a biomarker of lung cancer. J Cancer Res Clin Oncol. Nov. 2008;134(11):1191-7. doi: 10.1007/s00432-008-0402-6. Epub May 7, 2008.
Schena, et al. Quantitative monitoring of gene expression patterns with a complementary DNA microarray. Science. Oct. 20, 1995;270(5235):467-70.
Valladares-Ayerbes, et al. Evaluation of plakophilin-3 mRNA as a biomarker for detection of circulating tumor cells in gastrointestinal

(56) References Cited

OTHER PUBLICATIONS cancer patients. Cancer Epidemiol Biomarkers Prev. Jun. 2010;19(6):1432-40. doi: 10.1158/1055-9965.EPI-10-0123. Epub May 25, 2010.

Van Ham, et al. Urinary granzyme A mRNA is a biomarker to diagnose subclinical and acute cellular rejection in kidney transplant recipients. Kidney International (2010) 78, 1033-1040; doi:10.1038/ki.2010.274.

Vijayendran, et al. A quantitative assessment of heterogeneity for surface-immobilized proteins. Anal Chem. Feb. 1, 2001;73(3):471-80.

Wetmur. DNA probes: applications of the principles of nucleic acid hybridization. Crit Rev Biochem Mol Biol. 1991;26(3-4):227-59.

Wu, et al. Diagnostic devices as biomaterials: a review of nucleic acid and protein microarray surface performance issues. J Biomater Sci Polym Ed. 2008;19(6):725-53. doi: 10.1163/156856208784522092.

Wu, et al. The ligation amplification reaction (LAR)—amplification of specific DNA sequences using sequential rounds of template-dependent ligation. Genomics. May 1989;4(4):560-9.

Yamada, et al. Lymphocyte metallothionein-mRNA as a sensitive biomarker of cadmium exposure. Ind Health. Jan. 2001;39(1):29-32.

Zhu, et al. Analysis of yeast protein kinases using protein chips. Nature Genetics. 2000; 26: 283-289. doi:10.1038/81576.

Aryani, et al., In Vitro application of fibonucleases: comparison of the effects on mRNA and miRNA stability. BMC Research Notes, 2015; 8(164):1-9.

Jung, et al., Robust MicroRNA stability in degraded RNA preparations from human tissue and cell samples. Clinical Chemistry, 2010; 56(6):998-1006.

Kondkar, et al., Utility of circulating MicroRNAs as clinical biomarkers for cardiovascular diseases. BioMed Research International, 2015; Article ID 821823, 10 Pages.

Liu, et al., MicroRNA expression profiling using microarrays. Nature Protocols, 2008; 3:563-578.

Minoura, et al., MicroRNA profiling is more stable than messenger RNA against RNA degradation. Cellular and molecular biology, May 2008; 2 Pages.

Wang, et al., Label-free hybridization detection of a single nucleotide mismatch by immobilization of molecular beacons on an agarose film. Nucelic acids research, 2002; 30(12):1-9.

EP19155784.2 Extended European Search Report dated Jul. 15, 2019.

Tyagi et al. Molecular Beacons: Probes that Fluoresce Upon Hybridization. Nature Biotechnology14(3):303-308 (Mar. 1996).

Ferreira de Souza, et al., Circulating mRNAs and miRNAs as candidate markers for the diagnosis and prognosis of prostate cancer. PLoS One, 2017; 12(9): 1-16. e0184094. https://doi.org/10.1371/journal.pone.0184094.

Ng, et al., Presence of Filterable and Nonfilterable mRNA in the Plasma of Cancer Patients and Healthy Individuals. Clinical Chemistry, 2002; 48(8): 1212-1217.

Pös, et al., Circulating cell-free nucleic acids: Characteristics and applications. European Journal of Human Genetics, 2018; 26:937-945.

\* cited by examiner

Panel A	Panel B

| MN DNA | TaqMan Probe | C(t) |
|---|---|---|
| P2s | BMP-4 | - |
| P2s | Beta-actin | - |
| Actb-human-1 | BMP-4 | - |
| Actb-human-1 | Beta-actin | 40.51 +/- 0.92 |

FIGURE 8

METHODS AND DEVICES FOR DETECTION AND ACQUISITION OF BIOMARKERS

CROSS-REFERENCE

This application is a continuation of U.S. patent application Ser. No. 14/106,661 filed Dec. 13, 2013 and claims the benefit of U.S. Provisional Patent Application Ser. No. 61/737,237 filed on Dec. 14, 2012, which is incorporated herein by reference in its entirety.

SEQUENCE LISTING

This disclosure includes a sequence listing submitted as a text file pursuant to 37 C.P.R. § 1.52(e)(v) named 45872-701-301_SL.txt, created on Feb. 13, 2014, with a size of 966 bytes, which is incorporated herein by reference.

BACKGROUND

Analysis of biomarkers is fast becoming the preferred method for early detection of disease, patient stratification and monitoring efficacy of treatment. Rapid and highly sensitive detection of changes in a biomarker is often technically impossible, or may require a cumbersome procedure involving multiple processing steps, necessitating large sample volumes and a prolonged diagnosis/prognosis timeline. The sample from a patient is often of a limited volume and not amenable to processing or to procedures requiring multiple steps that extend the processing time.

Current methods for detecting molecular biomarkers or biological analytes of interest for diagnostic applications rely primarily on extraction of body fluid (e.g., blood, interstitial tissue fluid) from a patient. It is from this sample of fluid that specific biomarkers are assayed. More recent inventions do not directly sample clinically relevant biomarkers from the site of application, but rather, require further processing of body fluids. Other diagnostic methodologies that are not based on molecular assaying, e.g., biopsies, are usually cumbersome and fraught with misdiagnosis risks due to their inherently visual and subjective nature. For localized, non-circulating biomarkers, however, this has often been the only diagnostic option to-date.

There is a need in the art for better means for detecting and analyzing biomarkers present in the body of subjects having or at risk of developing various diseases or disorders. The present invention addresses this and other needs.

SUMMARY OF THE INVENTION

In one aspect, the invention provides devices for detecting or extracting one or more biomarkers from a tissue or biological sample of a subject in situ. The devices can comprise an array of microneedles and a plurality of probes specific for the biomarkers, wherein the probes are covalently attached to the microneedles. In some of the devices, the probes are specific for different biomarkers, and each different probe is attached to a different microneedle. In some other devices, the same probe for a specific biomarker is attached to two or more microneedles. The microneedles in the devices can be made of a polymer, a metal, a ceramic or any other suitable material.

In some cases, the disclosure provides a device for detecting or extracting one or more biomarkers from an in situ tissue or biological sample of a subject, comprising one or more microneedles, and one or more probes specific for the biomarkers, wherein the probes are attached to the microneedles, via covalent or non-covalent linkage.

The device can comprise a first microneedle. The first microneedle can be covalently attached to a first probe, which is specific for a first biomarker. Alternatively, the first microneedle can be non-covalently attached to the first probe. Further, the first probe can be attached to a plurality of microneedles. In some cases, the invention provides a device comprising a first microneedle, wherein the first microneedle is covalently or non-covalently attached to a first probe specific for a first biomarker. In some cases, the first biomarker can be a polynucleotide. The first probe can be a polynucleotide complementary to the first biomarker. In other cases, the first biomarker can be a polypeptide, an antibody, a metabolite, or a small molecule. Further, the first probe can be a polynucleotide, a polypeptide, a protein, an antibody, a small molecule, or a biological receptor. In some cases, the first needle is formed on a substrate.

The device can further comprise a second probe, which is specific for a second biomarker. The second probe can be different from the first probe. The second probe can be covalently or non-covalently attached to the first microneedle. Alternatively, the second probe can be covalently or non-covalently attached to a second microneedle. The second biomarker can be a polynucleotide. The second probe can be a polynucleotide complementary to the second biomarker. The second biomarker can also be a polypeptide, an antibody, a metabolite, or a small molecule. Further, the second probe can be a polynucleotide, a polypeptide, a protein, an antibody, a small molecule, a biological receptor. In some cases, the first probe specifically binds to a first nucleotide polymorphism and the second probe specifically binds to a second nucleotide polymorphism. In some cases, the first and second probes are different antibodies each specific to a different epitope of the same biomarker.

In some cases, the device provides for a microneedle comprising a polymer, a metal or a ceramic. A first probe can be attached, covalently or non-covalently to a plurality of microneedles. A second probe and a plurality of other probes can be attached, covalently or non-covalently, to a plurality of microneedles.

Some devices of the invention are directed to detecting nucleic acid biomarkers. In these devices, the probes that can be conjugated to the microneedles are oligonucleotides or polynucleotides complementary to the biomarkers. Some of the devices employ microneedles that are fabricated with a thermoplastic polymer. The polynucleotide probes in the devices can be conjugated to the microneedles via many suitable linkages, including but not limited to a thiol/amino bifunctional linker or a poly(ethylene glycol) linker. In some cases, a device of the invention further comprises a compartment for amplifying and identifying the first and second biomarkers.

Some other devices of the invention are specifically designed for detection of peptide or protein biomarkers. In some of these devices, the probes immobilized on the microneedles are antibodies specific for the biomarkers. In various embodiments of the invention, a planar substrate is used to support the array of microneedles. The devices of the invention can additionally contain a means for amplifying the biomarkers detected by the probes.

The device can comprise a plurality of microneedles. The plurality of microneedles can comprise at least one microneedle that is covalently or non-covalently attached to at least one probe specific for a biomarker. The biomarker can be indicative of a specific condition, including but not limited to a skin or eye condition. In some cases, the biomarker can be indicative of a skin condition. In some examples, the skin condition is a skin cancer. In other cases, the biomarker can be indicative of an eye condition. In some examples, the eye condition is an eye cancer or eye inflammation.

In some cases, the disclosure provides a device comprising a plurality of microneedles, wherein the plurality of microneedles comprises at least one microneedle that is covalently or non-covalently attached to at least one probe specific for a biomarker and the biomarker is indicative of a skin or eye condition. In some cases, the biomarker is a polynucleotide, and the at least one probe is complementary to the biomarker. In some cases, the at least one probe comprises different polynucleotide probes specific to different nucleotide polymorphisms of the same biomarker. In some cases, the biomarker is a peptide or polypeptide, and the at least one probe is an antibody specific for the biomarkers. In some cases, the at least one probe comprises different antibodies specific to different epitopes of the same biomarker.

A device of the invention can comprise a plurality of probes specific for a plurality of different biomarkers, wherein the plurality of probes are attached to the same or to different microneedles. In some cases, at least two different probes are attached to the same microneedle. In some cases, the devices comprise at least two identical probes for a specific biomarker, wherein the at least two identical probes are attached to one or more microneedles.

Alternatively, the biomarker can also be obtained during an intraoperative procedure. The device can further comprise a sensor that emits an optical signal when the probe detects the biomarker. In some examples, the optical signal of the probe can change when the probe detects the biomarker.

In another aspect, the disclosure provides methods for detecting or amplifying one or more biomarkers from an in situ tissue in subject (e.g., skin, blood stream, tissue) or ex vivo tissue sample. The methods entail (a) preparing a plurality of microneedles to which a plurality of probes specific for the biomarkers are covalently attached, (b) contacting the microneedles with a tissue or a biological sample of the subject, and (c) detecting biomarkers that are bound to the probes on the microneedles.

In some cases, the disclosure provides a method for detecting one or more biomarkers from an in situ tissue or biological sample in a subject, comprising (a) contacting a microneedle with a tissue or biological sample of the subject, wherein the microneedle is attached to a set of probes, and wherein the probes bind to one or more biomarkers in situ; and (b) detecting the one or more biomarkers that are bound to the probes.

In some cases, the disclosure provides a device comprising a plurality of microneedles, wherein the plurality of microneedles comprise at least one microneedle that is covalently or non-covalently attached to a probe specific for a biomarker, wherein the probe comprises a sensor that emits an optical signal when the probe detects the biomarker. In some cases, the optical signal of the probe increases when it detects the biomarker. In some cases, the optical signal of the probe decreases when it detects the biomarker.

In some cases, the disclosure provides a method for detecting one or more biomarkers from an in situ tissue or biological sample in a subject, comprising (a) preparing a device comprising one or more microneedles to which one or more probes specific for the biomarkers are covalently attached; (b) contacting the microneedle device with the tissue or biological sample of the subject; and (c) detecting biomarkers that are bound to the probes on the microneedle array.

In some cases, the disclosure provides a method for detecting one or more biomarkers from an in situ tissue or biological sample in a subject, comprising: (a) contacting a microneedle device with a tissue or biological sample of the subject, wherein the microneedle device comprises one or more probes specific for the one or more biomarkers, wherein at least one probe comprises a sensor that emits a visual signal when the probe detects the biomarkers; and (b) detecting biomarkers based on the visual signal.

Alternatively, the method can comprise (a) contacting a microneedle device with a tissue or biological sample of the subject, and at least two probes specific for the one or more biomarker, wherein at least two probes specific for the biomarker are different, wherein the probes are attached to the microneedles, via covalent or non-covalent linkage, and (b) detecting biomarkers that are bound to the probes.

In some cases, the disclosure provides a method for detecting one or more biomarkers within a tissue of a subject, comprising (a) contacting a microneedle with the tissue of the subject in situ, wherein the tissue comprises an extracellular matrix, wherein the microneedle is covalently attached to a set of probes, and wherein the probes bind to a biomarker in situ; and (b) disrupting the extracellular matrix. In some cases, the extracellular matrix is disrupted by an enzymatic activity. In some cases the disrupting the extracellular matrix comprises applying ultrasonic energy to the extracellular matrix. In some cases, the extracellular matrix is disrupted by an electric potential.

In a further example, a method can comprise (a) contacting a microneedle device with the sample comprising an extracellular matrix, wherein the microneedle is covalently attached to a set of probes, and wherein the probes bind to a biomarker in situ; and (b) disrupting the extracellular matrix. Alternatively, the method can comprise disrupting the cellular membrane. In either example, the extracellular matrix or the cellular membrane can be disrupted by an enzymatic activity, an ultrasonic energy, or an electronic potential.

In yet another example, a method can comprise: (a) contacting a microneedle device with a tissue or biological sample of the subject, wherein the microneedle device comprises one or more probes specific for the one or more biomarkers; and (b) amplifying the biomarkers.

The biomarkers can be polynucleotides and the probes can be polynucleotides complementary to the biomarkers. In some cases, the probes can be different polynucleotide probes specific to different nucleotide polymorphisms of the same biomarker The biomarkers can be peptides or polypeptides and the probes can be antibodies specific for the biomarkers. In some cases, the probes can be different antibodies specific to different epitopes of the same biomarker.

For simultaneous detection of different biomarkers, the probes used in the methods can be made specific for the different biomarkers. The probes can be attached to a different microneedle, or the probes can be attached to the same microneedle. In some other embodiments, at least two microneedles can bear identical probes, or multiple probes can be used for detecting a specific biomarker.

The disclosure also provides a method of preparing a microneedle device comprising: (a) obtaining a solution comprising a mineral salt; (b) adding a probe and a microneedle to the solution; and (c) conjugating the probe to the microneedle within the solution. In some cases, the mineral salt is sodium chloride. In some cases the concentration of the mineral salt is less than 2.5 M.

Any suitable materials can be used in making the microneedle array used in these methods. Examples include but are not limited to a polymer, a metal or a ceramic. Some methods of the invention are intended for detection of nucleic acid biomarkers. In these methods, the employed probes are oligonucleotide or polynucleotide molecules with sequences that are complementary to that of the biomarkers. In some of the methods, the nucleic biomarkers captured by the microneedle device are detected and analyzed by PCR or quantitative real-time PCR (qRT-PCR). In some of the methods, the microneedles are made of a polymer, and the probes are attached to the microneedles via a thiol/amino bifunctional linker. Alternatively, the microneedles are made of stainless steel and coated with gold, and the probes are attached to the microneedles via a thiol linker. In some embodiments, the microneedles can be solid. Some other methods of the invention are intended for detection of peptide or polypeptide biomarkers. In these methods, the employed probes are molecules that are capable of specifically binding to the biomarkers, e.g., monoclonal antibodies. Upon capturing with the microneedle-conjugated antibodies, the peptide or protein biomarkers bound to the probes on the microneedles can be detected by addition of an oligonucleotide-tagged secondary antibody and subsequent PCR amplification of the conjugated tag.

In some cases, the method for detecting one or more polynucleotide biomarkers from a skin or eye tissue in a subject can comprise contacting a microneedle device with the skin or eye tissue of the subject. The method can further comprise contacting the microneedle device with a dermal capillary of the subject. In other cases, the method can comprise contacting a microneedle device with the tissue or biological sample of the subject during an intraoperative procedure. The tissue or biological sample can be from an organ selected from the group consisting of brain, heart, breast, liver, pancreas, spleen, bladder, stomach, lung, uterus, cervix, prostate, kidney, intestine, appendix, and colon. The method can further comprise contacting the microneedles to the margins of a tumor after the tumor is removed from the subject. In some cases, a method of the disclosure detects a biomarker that is present in the blood of a subject.

The disclosure also provides a method for conjugating a probe to a microneedle, wherein a mineral salt is added. Examples of mineral salts include but are not limited to lithium salts, potassium salts, sodium salts, magnesium salts, and calcium salts, often with a halide counter ion. In some cases, the mineral salt is sodium chloride. The mineral salt can be added at a concentration between about 0.1 M to 2.0 M. Further, the mineral salt can be added at a concentration between about 0.5 M to 1.5 M.

The various methods of the present invention can further comprise detecting one or more biomarkers from a reference tissue obtained from the subject. Some devices or methods of the invention are designed for detecting and acquiring biomarkers from the blood stream of a subject. In these embodiments, the probe-conjugated microneedle array is contacted with the subject's blood stream by piercing the skin of the subject.

In yet another aspect, the invention provides kits comprising any of the devices for detecting or extracting biomarkers described in this application. The kits can further comprise a set of reagents for a polymerase chain reaction. In some examples, the set of reagents can be for a reverse-transcriptase polymerase chain reaction. The kit can further comprise a holder, or written instructions for a use thereof.

In some cases, the disclosure provides a kit comprising: (a) a device, comprising a plurality of microneedles, wherein the plurality of microneedles comprise at least one microneedle that is covalently or non-covalently attached to a first specific for a biomarker; and (b) a set of reagents for a polymerase chain reaction. In some cases, the kit further comprises a holder. In some cases, the set of reagents comprises a polymerase enzyme, a buffer, and a control sample. In some cases, the kit further comprises written instructions for a use thereof.

In a further aspect, the invention provides a composition comprising a plurality of microneedles coated with a substrate capable of disrupting an extracellular matrix. In some cases, the substrate can be an enzyme. The enzyme can be selected from the group consisting of serine proteases, thiol proteases, and MMPs. Specific enzymes include papain, hyaluronidase, streptokinase, streptodornase, trypsin, chymotrypsin, alpha-chymotrypsin, alpha-amlyase, DNase, collagenase, and sutilain. In one example, the enzyme is hyaluronidase.

A further understanding of the nature and advantages of the present invention may be realized by reference to the remaining portions of the specification and claims.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also referred to as "Figures" or "FIGs.") of which:

FIG. 8 displays the qRT-PCR data from assaying a homogenized human skin sample using the methods of the present invention.

DETAILED DESCRIPTION

Figure 1:
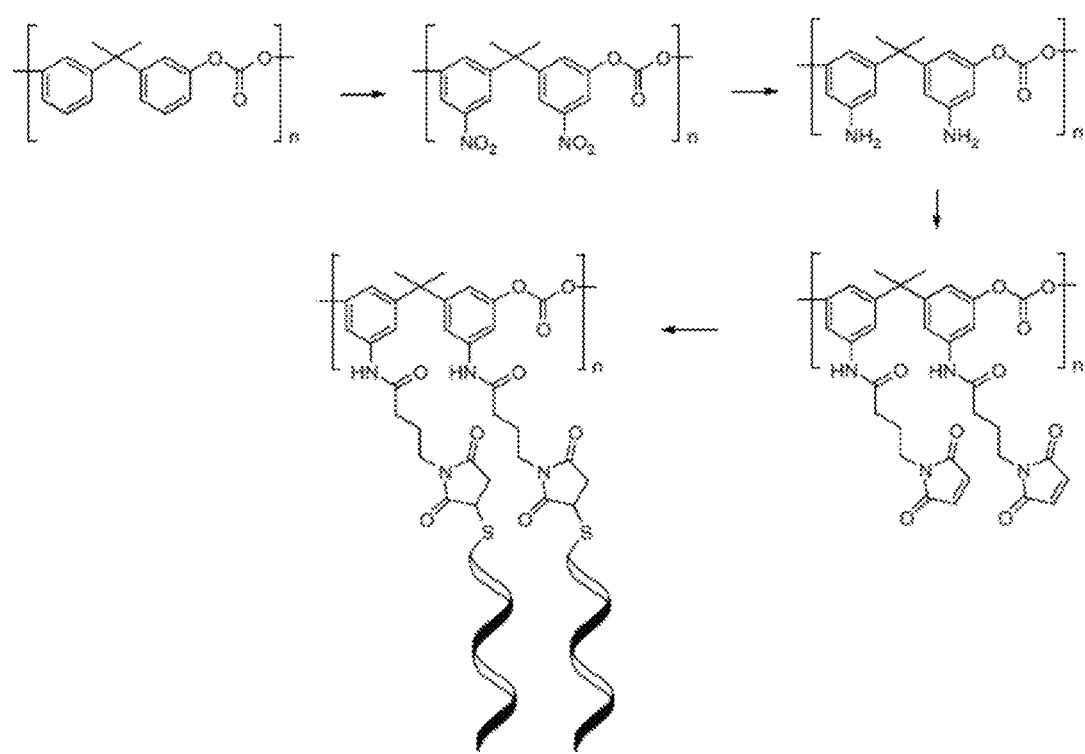
FIG. 1 illustrates the scheme of chemical modification of the surface of polycarbonate and attachment of thiol modified DNA probe.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed in practicing the invention.

The present invention provided devices and methods for detection and acquisition of biomarkers, especially molecular biomarkers, from the body of a subject. In some embodiments, microneedle array-based devices with a singular or plurality of microneedles are fabricated in accordance with the present invention. The length of individual microneedles on the array can vary, e.g., ranging from 50 µm to 5 mm. The devices can be fabricated by different materials, composites and material combinations, including, but not limited to, metals and metal alloys, inorganic ceramics and polymers. Microneedles are chemically modified to couple probes for biomarkers to the microneedle surface. The specific coupling chemistries depend on the material of the microneedles. Different biomarkers can be detected with cognate probes immobilized on the same array or the same microneedle. As exemplifications, the devices can be applied to patient on anatomical locations such as skin, eye, tumor or other tissue for the purposes of allowing the desired biomarkers to bind to the probes presented. Application can be done by hand (e.g., thumb pressure), an applicator device, with or without a strap or band to hold it in place for the duration of sampling. The physical insertion of microneedle probes can disrupt cell membranes to release genetic material, including biomarkers, that are available for binding to probes on the inserted microneedles. Extracellular biomarkers are directly available for binding to probes, and do not need to be sampled from materials released from disrupted cells.

The time needed for biomarkers to bind to the microneedles will depend on a number of parameters, including, but not limited to, the prevalent quantity, biodistribution and concentration of biomarkers, tissue organization, and the physical and chemical dimensions of microneedle probes (e.g., surface area, number of probes, number of binding sites). Application time can range, e.g., from less than 10 seconds to 60 minutes. Upon removal of the microneedle arrays from tissue, biomarkers can be assayed using a number of different techniques, including, but not limited to, PCR, quantitative PCR, protein PCR, sandwich ELISA, elution mass spectroscopy, elution Western blot, and elution ELISA. Biomarkers can be assayed either after separation from microneedles, or directly on the microneedles.

As illustrated in detail in the Examples, depending on the microneedles and the probes to be coupled, various chemistries can be used in the conjugation of the probes to the microneedles. Chemical modifications of microneedles made of polymer for covalent attachment of biomolecules can be performed with numerous linkages that have been developed in the art. For example, for microneedles with a polycarbonate surface, the carbonate monomer contains aromatic moieties that can be chemically derivatized post-polymerization. Treatment of needles with nitric acid, followed by reduction of the resulting nitro group gives an amine handle through which molecules can be coupled to the polymer backbone. Importantly, this two-step reaction can be performed on manufactured microneedle arrays without compromising the integrity of the array or individual microneedles. Using this procedure, standard amide bond coupling reagents can be used to link a carboxylic acid-containing probe to the microneedle surface.

When the microneedles are fabricated with metal, application of the same principles as described for polymer surfaces to metal surfaces is attainable. For example, stainless steel surfaces can be coated with gold via a sputter coating process, providing a chemical handle for attachment. By utilizing the well-characterized affinity of thiols for gold surfaces, one can then attach a bivalent crosslinker with a thiol on one terminus and an amine on the other to the metal surface, thereby allowing for identical coupling chemistries of the probe molecule to the microneedle surface. Suitable methods for chemical modifications of other types of microneedle surfaces (e.g., inorganic ceramic) for covalent linkage of biological molecules are also known in the art.

The invention described herein has broad applicability in many different aspects of diagnostics, including genetic (e.g., mRNA, DNA), protein, hormonal, small molecule and cellular biomarkers for diagnostics and disease prognosis. For example, the devices or methods described herein can be useful in detection of skin-based biomarkers, detection of systemically circulating biomarkers, pathogen detection (e.g., bacteria, viruses or parasites), or determination of tumor margins during surgical tumor resection. As described herein, specific examples of skin-based diagnostic applications of the invention include detection of biomarkers for cutaneous malignant melanoma, non-melanocyte skin cancers (e.g., basal cell carcinoma, squamous cell carcinoma), autoimmune disorders (e.g., psoriasis), infectious diseases, and tropical diseases (e.g., Buruli ulcer, onchocerciasis). Specific examples of non-skin based diagnostic applications of the invention include detection of markers for oncologic diseases, hematologic diseases, cardiovascular diseases, Down's syndrome, and real-time, rapid biomarker detection during clinical trials.

The following sections provide more detailed guidance for practicing the present invention.

Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1st ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3rd ed., 2002); *Dictionary of Chemistry*, Hunt (Ed.), Routledge (1st ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press (4th ed., 2000). In addition, the following definitions are provided to assist the reader in the practice of the invention.

Biomarkers broadly refer to any characteristics that are objectively measured and evaluated as indicators of normal biological processes, pathogenic processes, or pharmacologic responses to therapeutic intervention. Unless otherwise noted, the term biomarker as used herein specifically refers to biomarkers that have biophysical properties, which allow their measurements in biological samples (e.g., plasma, serum, cerebrospinal fluid, bronchoalveolar lavage, biopsy). Unless otherwise noted, the term biomarker is used interchangeably with "molecule biomarker" or "molecular markers." Examples of biomarkers include nucleic acid biomarkers (e.g., oligonucleotides or polynucleotides), peptides or protein biomarkers, lipids, and lipopolysaccharide markers.

As used herein, microneedle devices or microneedle arrays (microarrays) refer to a device comprising at least one small piercing element or microneedle onto which is immobilized a diagnostic agent or compound. The microneedle is capable of piercing the biological barriers in human or other mammalian subjects (e.g., the stratum corneum of the skin) upon contact. Preferably, the device comprises a plurality of such microneedles, e.g., 2, 5, 10, 25, 50, 100, 150, 200, 250, 300, 350, 400, 450, 500, 550, 600, 650, 700, 750, 800, 850, 900, 950, 1000, 2000, 5000, 10000, 20000, or more. By conjugating diagnostic probes to the microneedles, the microneedle devices of the invention provide a means for in situ detection of biomarkers in a tissue or biological sample of a subject (e.g., blood stream or skin).

The term "polynucleotide" or "nucleic acid" as used herein refers to a polymeric form of nucleotides of any length, either ribonucleotides or deoxyribonucleotides, that comprise purine and pyrimidine bases, or other natural, chemically or biochemically modified, non-natural, or derivatized nucleotide bases. Polynucleotides of the embodiments of the invention include sequences of deoxyribonucleic acid (DNA), ribonucleic acid (RNA), or DNA copies of ribonucleic acid (cDNA), all of which may be isolated from natural sources, recombinantly produced, or artificially synthesized. A further example of a polynucleotide is polyamide polynucleotide (PNA). The polynucleotides and nucleic acids may exist as single-stranded or double-stranded. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components. The polymers made of nucleotides such as nucleic acids, polynucleotides and polynucleotides may also be referred to herein as nucleotide polymers.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 15-25 or more nucleotides, although it may contain fewer nucleotides. The factors involved in determining the appropriate length of primer are readily known to one of ordinary skill in the art.

Polypeptides are polymer chains comprised of amino acid residue monomers which are joined together through amide bonds (peptide bonds). The amino acids may be the L-optical isomer or the D-optical isomer. In general, polypeptides refer to long polymers of amino acid residues, e.g., those consisting of at least more than 10, 20, 50, 100, 200, 500, or more amino acid residue monomers. A polypeptide can be a chain of at least two amino acids, peptide-mimetics, a protein, a recombinant protein, an antibody (monoclonal or polyclonal), an antibody fragment, an antigen, an epitope, an enzyme, a receptor, a vitamin, or a structure analogue or combinations thereof. However, unless otherwise noted, the term polypeptide as used herein also encompass short peptides which typically contain two or more amino acid monomers, but usually not more than 10, 15, or 20 amino acid monomers.

Proteins are long polymers of amino acids linked via peptide bonds and which may be composed of two or more polypeptide chains. More specifically, the term "protein" refers to a molecule composed of one or more chains of amino acids in a specific order; for example, the order as determined by the base sequence of nucleotides in the gene coding for the protein. Proteins are essential for the structure, function, and regulation of the body's cells, tissues, and organs, and each protein has unique functions. Examples are hormones, enzymes, and antibodies. In some embodiments, the terms polypeptide and protein may be used interchangeably.

"Biological sample" as used herein is a sample of biological tissue or chemical fluid that is suspected of containing a biomarker or an analyte of interest. The sample may be an ex vivo sample or in vivo sample. Samples include, for example, body fluids such as whole blood, serum, plasma, cerebrospinal fluid, urine, lymph fluids, and various external secretions of the respiratory, intestinal and genitourinary tracts such as tears, saliva, semen, milk, and the like; and other biological fluids such as cell culture suspensions, cell extracts, cell culture supernatants. Samples may also include tissue biopsies, e.g., from the lung, liver, brain, eye, tongue, colon, kidney, muscle, heart, breast, skin, pancreas, uterus, cervix, prostate, salivary gland, and the like. Samples may also be microbiopsies, small samples or even single cells extracted from patients and subsequently processed, for example, using laser capture microdisection. A sample may be suspended or dissolved in, e.g., buffers, extractants, solvents, and the like.

As used herein, "tissue" refers to a collection of similar cells and the intracellular substances surrounding them. There are four basic tissues in the body: 1) epithelium; 2) connective tissues, including blood, bone, and cartilage; 3) muscle tissue; and 4) nerve tissue.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5.

A covalent bond is a chemical bond that involves the sharing of electron pairs between atoms. Covalent bonding includes many kinds of interactions, including σ-bonding, π-bonding, metal-to-metal bonding, agostic interactions, and three-center two-electron bonds. A non-covalent interaction differs from a covalent bond in that it does not involve the sharing of electrons. A non-covalent bond can be generally classified into 4 categories: electrostatic, π-effects, van der Waals forces, and hydrophobic effects.

Biomarkers.

The devices or methods described herein can be employed in various diagnostic applications for detecting and capturing specific biomarkers. Biomarkers can be used in clinical practice to identify risk for or diagnose a disease, stratify patients, assess disease severity or progression, predict prognosis, or guide treatment. In drug development biomarkers may be used to help determine how a drug works in the body, to determine a biologically effective dose of a drug, to help assess whether a drug is safe or effective, and to help identify patients most likely to respond to a treatment, or are least likely to suffer an adverse event when treated with a drug. Biomarkers can sometimes be used as part of the approval process for a drug or treatment, to inform regulatory decision-making.

In some cases, employing the microneedle array device described herein and routinely practiced amplification technologies (e.g., genomics or proteomics technologies), various biomarkers in the body of a subject can be detected with the methods and devices of the present invention. In some cases, various biomarkers from the subject can be detected using the microneedle array device to capture a biomarker or set of biomarker and then using one or more additional tagged probes to detect the captured biomarkers.

The biomarkers that can be detected with the present disclosure include nucleic acid-based biomarkers (DNA, RNA, mRNA transcripts, genomic DNA, tRNA, siRNA, miRNA, mitochondrial DNA, mitochondrial RNA, exosomal nucleic acids, cell-free DNA or RNA, polynucleotides carrying mutated genes and polymorphisms), peptides, proteins, lipids, lipids metabolites, and small molecules. The biomarkers include diagnostic biomarkers (e.g., cardiac troponin for the diagnosis of myocardial infarction), staging of disease biomarkers (e.g., brain natriuretic peptide for congestive heart failure), disease prognosis biomarkers (cancer biomarkers), and biomarkers for monitoring the clinical response to an intervention (HbAlc for anti-diabetic treatment). They also include biomarkers used in decision making in early drug development. For instance, pharmacodynamic (PD) biomarkers are markers of a certain pharmacological response, which are of special interest in dose optimization studies. Examples of biomarkers that have disease implications include serum LDL for high cholesterol and blood pressure, P53 gene and MMPs for cancer. Additional examples of specific nucleic acid biomarkers and protein biomarkers that are suitable for detection with methods and devices of the present invention are described below.

Some preferred embodiments of the invention are directed to detection and amplification of nucleic acid biomarkers. Many nucleic acid biomarkers are known in the art. Examples include telomerase reverse transcriptase mRNA as a diagnostic biomarker for hepatocellular carcinoma (Miura et al., Clin. Cancer Res. 11:3205-9, 2005), plasma hnRNP B1 mRNA as a biomarker of lung cancer (Sato et al., J. Cancer Res. Clin. Oncol. 134:1191-7, 2008), GD2/GM2 synthase mRNA as a biomarker for small cell lung cancer (Chen et al., Lung Cancer. 67:216-20, 2010), serum transforming growth factor-alpha mRNA as a prognosis biomarker for fulminant hepatitis (Miura et al., Hepatol Int. 2:213-21, 2008), Plakophilin-3 mRNA for gastrointestinal cancer (Valladares-Ayerbes et al., Cancer Epidemiol Biomarkers Prev. 19:1432-1440, 2010), metallothionein as a biomarker of heavy metal exposure (Yamada et al., Industrial Health 39:29-32, 2001), WT1 mRNA as a biomarker for monitoring minimal residual disease in acute myeloid leukemia (Sakamoto et al., Tohoku J Exp Med. 219:169-76, 2009), and granzyme A mRNA as a biomarker for kidney transplant rejection (van Ham et al., Kidney Int'l. Aug. 18, 2010). These biomarkers, as well as various other nucleic acid biomarkers known in the art, are all suitable for detection with methods and devices of the present invention. Polynucleotide sequences of these known biomarkers were already described and characterized in the art. Based on their known sequences, probes specific for detecting these biomarkers (e.g., oligonucleotide primers) can be easily designed and synthesized with routinely practiced methods of molecular biology. See, e.g., Sambrook et al., *Molecular Cloning: A Laboratory Manual*, Cold Spring Harbor Press, N.Y., ($3^{rd}$ ed., 2000); and Brent et al., *Current Protocols in Molecular Biology*, John Wiley & Sons, Inc. (ringbou ed., 2003).

In some other embodiments, peptides or protein biomarkers are detected with the devices and methods of the invention. Methods and devices described herein are useful for detection of various peptide or protein biomarkers that have been characterized in the art. Specific examples of peptide or protein biomarkers suitable for the invention include, but are not limited to, PSA as a biomarker of prostate cancer (Polascik et al., J. Urol. 162:293-306, 1999), cancer antigen 125 (CA125) as a biomarker for ovarian cancer (Jacobs et al., Lancet 353:1207-1210, 1999), BC1, BC2 and BC3 as serum biomarkers for detection of breast cancer (Mathelin et al., Breast Cancer Res. Treat. 96:83-90, 2006), β-Defensin-2 Protein as a serum biomarker for psoriasis (Patrick et al., PLoS ONE 4: e4725, 2009), C-reactive protein as a biomarker of metastasis of renal cell carcinoma (Johnson et al., Mol. Diagn. Ther. 14:191-3, 2010), high molecular weight-melanoma-associated antigen as a biomarker of desmoplastic melanoma (Goto et al., Pigment Cell Melanoma Res. 23: 137-140, 2010), telomerase expression as a biomarker of malignant transformation in patients with inflammatory bowel disease (Gonzalo et al., Gastroenterol Hepatol. 33:288-96, 2010), and insulin-like growth factor II mRNA-binding protein 3 (IMP3) as a prognostic biomarker for oral squamous cell carcinoma (Li et al., Head Neck. Jul. 22, 2010). Probes for detecting these biomarkers (e.g., monoclonal antibodies) can be readily generated with standard immunology techniques (e.g., hybridoma technology) or obtained from commercial suppliers (e.g., Abnova Corporation, Full Moon BioSystems and Spring Bioscience).

Depending on the specific type of biomarkers to be detected, the microneedle device described herein can be combined with various methods known in the art for amplifying and examining molecular entities. Many genomic and proteomics techniques are suitable for use in the device and methods of the invention for detecting and analyzing protein and nucleic acid markers. For example, PCR can be used for amplifying and examining nucleic acid molecules bound to the probes on the microneedles. ELISA can be used for analyzing peptide or protein markers captured by the microneedle-based device of the invention. Apart from genomics and proteomics platforms biomarker assay technique, metabolomics, lipidomics, and glycomics techniques can also be used in the identification and detection of biomarkers of other chemical classes. For example, mass spectrometry, chromatography, and nuclear magnetic resonance are useful for detecting and analyzing various biological molecules bound to the microneedles.

Microneedles for Attaching Diagnostic Probes.

Figure 4:
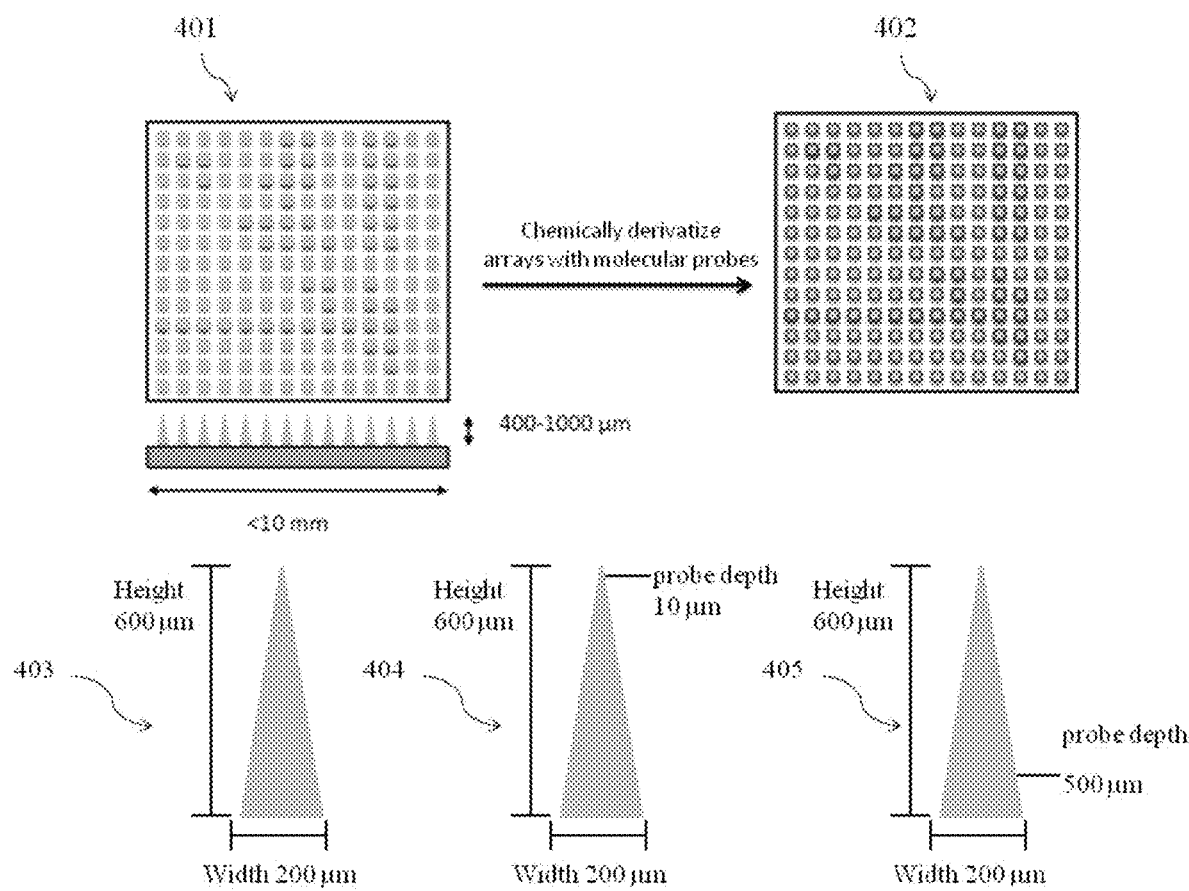
FIG. 4 is a diagram of a surface of a device of the disclosure with a plurality of microneedles.

The invention provides microneedle devices with covalently attached molecular probes for detection and acquisition of biomarkers from a subject in situ. The microneedle based device contains one or more microneedles that can be pierced into mammalian biological barriers such as the skin or mucous membrane. Often, the microneedles are non-invasive, or minimally-invasive. When a plurality of microneedles is present, the device can also have a planar substrate which supports the microneedles. The substrate can be made of the same material as that of the microneedle. It can also be made of a different material. The microneedles employed in the invention have a length (height) that is typically in the range of 20 µm to 1 mm, preferably in the range of 50 µm to 500 µm. FIG. 4 is a diagram of a surface of a device of the invention comprising a plurality of microneedles. Each "square" in 401 illustrates an individual microneedle. 401 illustrates a plurality of microneedles on a surface of a device of the invention, wherein the height of the needles ranges from about 400 µm to about 1000 µm. In some embodiments, the height of the needles is from about 20 µm to about 50 µm, from about 20 µm to about 100 µm, from about 20 µm to about 150 µm, from about 20 µm to about 200 µm, from about 20 µm to about 250 µm, from about 20 µm to about 300 µm, from about 20 µm to about 350 µm, from about 20 µm to about 400 µm, from about 20 µm to about 450 µm, from about 20 µm to about 500 µm, from about 20 µm to about 550 µm, from about 20 µm to about 600 µm, from about 20 µm to about 650 µm, from about 20 µm to about 700 µm, from about 20 µm to about 750 µm, from about 20 µm to about 800 µm, from about 20 µm to about 850 µm, from about 20 µm to about 900 µm, from about 20 µm to about 950 µm, or from about 20 µm to about 1 mm. In some cases, the height of the microneedles is less than 1 µm, less than 5 µm, less than 10 µm, less than 15 µm, less than 20 µm, less than 25 µm, less than 30 µm, less than 35 µm, less than 40 µm, less than 45 µm, less than 50 µm, less than 75 µm, less than 100 µm, less than 150 µm, less than 200 µm, less than 250 µm, less than 300 µm, less than 500 µm, less than 750 µm, less than 1000 µm, less than 2000 µm, less than 3000 µm, less than 4000 µm, less than 5000 µm, less than 7500 µm or less than 10000 µm. In some cases, the height of the microneedles is greater than 1 µm, greater than 5 µm, greater than 10 µm, greater than 15 µm, greater than 20 µm, greater than 25 µm, greater than 30 µm, greater than 35 µm, greater than 40 µm, greater than 45 µm, greater than 50 µm, greater than 75 µm, greater than 100 µm, greater than 150 µm, greater than 200 µm, greater than 250 µm, greater than 300 µm, greater than 500 µm, greater than 750 µm, greater than 1000 µm, greater than 2000 µm, greater than 3000 µm, greater than 4000 µm, greater than 5000 µm, greater than 7500 µm or greater than 10000 µm.

While the needle-shaped microneedles can be blunt-pointed objects, they are preferably sharp-pointed objects. In some embodiments, the microneedles have a circular cone structure with a diameter of the base generally in the range of 10 µm to 500 µm, preferably in the range of 20 µm to 200 µm. 401 illustrates a surface of a device of the invention with a plurality of microneedles wherein the diameter of the base is less than 10 mm in width. For devices containing a plurality of microneedles, the microneedles can be present on the devices in rows. In some embodiments, the rows can be spaced at virtually equal intervals to the space of the needles aligned in the row. In some embodiments, the rows can be spaced at irregular intervals.

A microneedle can have a plurality of shapes, for example, a microneedle can be round, conical, triangular, square, rectangular, pentagonal, hexagonal, heptagonal, octagonal, or any other suitable shape. A microneedle can be a sharp microneedle, a blunt microneedle, or any combination thereof. For example, a device of the invention comprising a plurality of sharp microneedles can be used to penetrate the skin of a subject thereby contacting the probe(s) on the microneedle with, for example, an RNA biomarker. A sharp microneedle can be used to disrupt tissue of a biological sample, such as a layer of cells or the outer membrane of a cell. A blunt microneedle can be used to touch the surface of the skin of a subject thereby contacting the microneedle with, for example, a cell-surface biomarker on the skin. In some cases, this disclosure provides microneedle devices that comprise microneedles with different shapes (e.g., sharp and blunt microneedles).

In some embodiments, a device of the invention comprises at least 1 microneedle, at least 100 microneedles, at least 200 microneedles, at least 300 microneedles, at least 400 microneedles, at least 500 microneedles, at least 600 microneedles, at least 700 microneedles, at least 800 microneedles, at least 900 microneedles, at least 1000 microneedles, at least 1100 microneedles, at least 1200 microneedles, at least 1300 microneedles, at least 1400 microneedles, at least 1500 microneedles, at least 1600 microneedles, at least 1700 microneedles, at least 1800 microneedles, at least 1900 microneedles, at least 2000 microneedles, at least 2100 microneedles, at least 2200 microneedles, at least 2300 microneedles, at least 2400 microneedles, at least 2500 microneedles, at least 2600 microneedles, at least 2700 microneedles, at least 2800 microneedles, at least 2900 microneedles, at least 3000 microneedles, at least 3100 microneedles, at least 3200 microneedles, at least 3300 microneedles, at least 3400 microneedles, at least 3500 microneedles, at least 3600 microneedles, at least 3700 microneedles, at least 3800 microneedles, at least 3900 microneedles, at least 4000 microneedles, at least 4100 microneedles, at least 4200 microneedles, at least 4300 microneedles, at least 4400 microneedles, at least 4500 microneedles, at least 4600 microneedles, at least 4700 microneedles, at least 4800 microneedles, at least 4900 microneedles, or at least 5000 microneedles.

In some embodiments, a device of the invention comprises at most 10000 microneedles, at most 5000 microneedles, at most 2500 microneedles, at most 2000 microneedles, at most 1000 microneedles, at most 500 microneedles, at most 400 microneedles, at most 300 microneedles, at most 100 microneedles, at most 90 microneedles, at most 50 microneedles, at most 40 microneedles, at most 30 microneedles, at most 20 microneedles, at most 15 microneedles, at most 10 microneedles, at most 9 microneedles, at most 8 microneedles, at most 7 microneedles, at most 6 microneedles, at most 5 microneedles, at most 4 microneedles, at most 3 microneedles, at most 2 microneedles, or 1 microneedle.

In some embodiments, a device of the invention comprises from about 1 microneedle to about 100 microneedles, from about 1 microneedle to about 200 microneedles, from about 1 microneedle to about 300 microneedles, from about 1 microneedle to about 400 microneedles, from about 1 microneedle to about 500 microneedles, from about 1 microneedle to about 600 microneedles, from about 1 microneedle to about 700 microneedles, from about 1 microneedle to about 800 microneedles, from about 1 microneedle to about 900 microneedles, from about 1 microneedle to about 1000 microneedles, from about 1 microneedle to about 1100 microneedles, from about 1 microneedle to about 1200 microneedles, from about 1 microneedle to about 1300 microneedles, from about 1 microneedle to about 1400 microneedles, from about 1 microneedle to about 1500 microneedles, from about 1 microneedle to about 1600 microneedles, from about 1 microneedle to about 1700 microneedles, from about 1 microneedle to about 1800 microneedles, from about 1 microneedle to about 1900 microneedles, from about 1 microneedle to about 2000 microneedles, from about 1 microneedle to about 2100 microneedles, from about 1 microneedle to about 2200 microneedles, from about 1 microneedle to about 2300 microneedles, from about 1 microneedle to about 2400 microneedles, from about 1 microneedle to about 2500 microneedles, from about 1 microneedle to about 2600 microneedles, from about 1 microneedle to about 2700 microneedles, from about 1 microneedle to about 2800 microneedles, from about 1 microneedle to about 2900 microneedles, from about 1 microneedle to about 3000 microneedles, from about 1 microneedle to about 3100 microneedles, from about 1 microneedle to about 3200 microneedles, from about 1 microneedle to about 3300 microneedles, from about 1 microneedle to about 3400 microneedles, from about 1 microneedle to about 3500 microneedles, from about 1 microneedle to about 3600 microneedles, from about 1 microneedle to about 3700 microneedles, from about 1 microneedle to about 3800 microneedles, from about 1 microneedle to about 3900 microneedles, from about 1 microneedle to about 4000 microneedles, from about 1 microneedle to about 4100 microneedles, from about 1 microneedle to about 4200 microneedles, from about 1 microneedle to about 4300 microneedles, from about 1 microneedle to about 4400 microneedles, from about 1 microneedle to about 4500 microneedles, from about 1 microneedle to about 4600 microneedles, from about 1 microneedle to about 4700 microneedles, from about 1 microneedle to about 4800 microneedles, from about 1 microneedle to about 4900 microneedles, or from about 1 microneedle to about 5000 microneedles.

The substrate and the microneedles of the arrays can be made of various biodegradable or non-biodegradable materials. Examples of the material for the microneedles or substrate include poly(methyl methacrylate), silicon, silicon dioxide, ceramic, metal (such as stainless steel, titanium, nickel, molybdenum, chromium, and cobalt), and synthetic or natural resin material. Some embodiments use a biodegradable polymer such as polylactic acid, polyglycolide, polylactic acid-co-polyglycolide, pullulan, capronolactone, polyurethane or polyanhydride. In some other embodiments, a non-degradable material is employed to fabricate the microneedle array, e.g., a polymer polycarbonate, a synthetic or natural resin material such as polymethacrylic acid, ethylenevinylacetate, polytetrafluoroethylene, polysulfone, or polyoxymethylene. In some embodiments, the employed material comprises or is coated with a polysaccharide such as hyaluronic acid, pullulan, dextran, dextrin or chondroitin sulfate. In some cases, the microneedle is fabricated with a thermoplastic polymer.

The substrate and the microneedles of the arrays can be made of various thermoplastic polymers. Non-limiting examples of thermoplastic polymers include acrylic polymers, such as poly(methyl methacrylate) (PMMA), nylon, polyethylene, polypropylene, polystyrene, polyvinyl chloride, or Teflon. In some cases, a device of the invention is fabricated with a thermoplastic polymer selected from the group consisting of polycarbonate, poly(methyl methacrylate), polyethylene and polypropylene.

Non-limiting examples of non-degradable polymers include, for example, silicone, hydrogels such as crosslinked poly(vinyl alcohol) and poly(hydroxy ethylmethacrylate), ethylene-vinyl acetate, acyl substituted cellulose acetates and alkyl derivatives thereof, partially and completely hydrolyzed alkylene-vinyl acetate copolymers, unplasticized polyvinyl chloride, crosslinked homo- and copolymers of polyvinyl acetate, crosslinked polyesters of acrylic acid and/or methacrylic acid, polyvinyl alkyl ethers, polyvinyl fluoride, polycarbonate, polyurethane, polyamide, polysulphones, styrene acrylonitrile copolymers, crosslinked poly (ethylene oxide), poly(alkylenes), poly(vinyl imidazole), poly(esters), poly(ethylene terephthalate), polyphosphazenes, and chlorosulphonated polyolefines, and combinations thereof. In some embodiments the polymer comprises ethylene vinyl acetate.

Non-limiting example of biodegradable polymers include polyesters such as 3-hydroxypropionate, 3-hydroxybutyrate, 3-hydroxyvalerate, 3-hydroxycaproate, 3-hydroxyheptanoate, 3-hydroxyoctanoate, 3-hydroxynonanoate, 3-hydroxydecanoate, 3-hydroxyundecanoate, 3-hydroxydodecanoate, 4-hydroxybutyrate, 5-hydroxyvalerate, polylactide or polylactic acid including poly(d-lactic acid), poly(l-lactic acid), poly(d,l-lactic acid), polyglycolic acid and polyglycolide, poly(lactic-co-glycolic acid), poly(lactide-co-glycolide), poly(ε-caprolactone) and polydioxanone. Polysaccharides including starch, glycogen, cellulose and chitin can also be used as biodegradable materials.

402 illustrates a surface of a device of the disclosure 401 comprising a plurality of microneedles that have been coupled with at least one type of probe. 402 can be coupled with, for example, a polynucleotide probe, a peptide probe, a protein probe, or any combination thereof. A probe attached to a microneedle on a device 402 can be covalently or non-covalently coupled to the microneedle. Examples 1 and 2 describe in further detail various methods for covalently coupling a probe to a surface.

A distance between the center of two microneedles on a device of the disclosure can be calculated to determine a density of the microneedles in the device. In some embodiments, the center-to-center distance between two microneedles can be less than 1000 μm, less than 900 μm, less than 800 μm, less than 700 μm, less than 600 μm, less than 500 μm, less than 400 μm, less than 300 μm, less than 200 μm, or less 100 μm. In some embodiments, the center-to-center distance between two microneedles can be no greater than 100 μm, no greater than 200 μm, no greater than 300 μm, no greater than 400 μm, no greater than 500 μm, no greater than 600 μm, no greater than 700 μm, no greater than 800 μm, no greater than 900 μm, or no greater than 1000 μm.

A microneedle of the disclosure can comprise a plurality of different diameters or base widths. The shape of the base of a microneedle can be, for example, round, rectangular, triangular, square, pentagonal, hexagonal, heptagonal, or other geometric shape. A microneedle of the disclosure can have a diameter or base width that is no greater than 500 μm, no greater than 400 μm, no greater than 300 μm, no greater than 200 μm, no greater than 100 μm, no greater than 50 μm, no greater than 40 μm, no greater than 30 μm, no greater than 20 μm, no greater than 10 μm, no greater than 1000 nm, no greater than 900 nm, no greater than 800 nm, no greater than 700 nm, no greater than 600 nm, no greater than 500 nm, no greater than 400 nm, no greater than 300 nm, no greater than 200 nm, or no greater than 100 nm.

A probe can be covalently or non-covalently attached to a microneedle at a plurality of different depths within the microneedle. 403 illustrates a microneedle with a height of 600 μm and a width of 200 μm. 404 illustrates a microneedle with a height of 600 μm and a width of 200 μm and a covalently attached probe at a depth of 10 μm. 405 illustrates a microneedle with a height of 600 μm and a width of 200 μm and a covalently attached probe at a depth of 500 μm. In some cases the depth of a probe within a microneedle can be used to determine a depth in the tissue where a biomarker can be found. In some cases, a device comprising a plurality of microneedles with a plurality of probes attached at different depths of different microneedles can be used to determine where in a tissue a biomarker can be found. For example, the device can be used to determine the size or depth of a lesion, such as a cancerous lesion.

A depth of a probe can be of about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, about 400 μm, about 410 μm, about 420 μm, about 430 μm, about 440 μm, about 450 μm, about 460 μm, about 470 μm, about 480 μm, about 490 μm, about 500 μm, about 510 μm, about 520 μm, about 530 μm, about 540 μm, about 550 μm, about 560 μm, about 570 μm, about 580 μm, about 590 μm, about 600 μm about 610 μm, about 620 μm, about 630 μm, about 640 μm, about 650 μm, about 660 μm, about 670 μm, about 680 μm, about 690 μm, about 700 μm, about 710 μm, about 720 μm, about 730 μm, about 740 μm, about 750 μm, about 760 μm, about 770 μm, about 780 μm, about 790 μm, about 800 μm, about 810 μm, about 820 μm, about 830 μm, about 840 μm, about 850 μm, about 860 μm, about 870 μm, about 880 μm, about 890 μm, about 900 μm, of about 910 μm, about 920 μm, about 930 μm, about 940 μm, about 950 μm, about 960 μm, about 970 μm, about 980 μm, about 990 μm, or about 1000 μm.

Optionally, the microneedle devices of the invention can additionally contain an applicator unit that can be used to apply the device to a subject. The applicator unit can control various application parameters, such as the speed with which the array is applied, the force with which the array is applied, and/or the angle with which the array impacts a tissue of the subject (e.g., the skin). In addition, the applicator may aid in handling or otherwise transferring the array from a storage unit to the subject. In some embodiments, the applicator can be a single-use, disposable tool that serves as both a storage unit and an application tool. Examples of suitable applicators and methods of application of microneedle arrays are disclosed in U.S. Pat. No. 6,293,925 (Safabash et al.), U.S. Pat. No. 6,743,211 (Prausnitz et al.), U.S. Pat. No. 6,881,203 (Delmore et al.), and U.S. Pat. No. 6,855,131 (Trautman et al.), and United States Patent Application Publication Nos. 2004/0181203 (Cormier et al.), 2002/0032415 (Trautman et al.), and 2002/0087182 (Trautman et al.). The applicator unit can have a plurality of different shapes. In some embodiments, the applicator unit can be, for example, linear, triangular, rectangular, or disk-shaped. In some embodiments, the applicator unit is a pen applicator.

The microneedle arrays for conjugating diagnostic probes can be readily produced using materials and methods well known in the art for fabricating arrays with microprotrusion structures. See, e.g., U.S. Pat. Nos. 7,416,541, 7,332,197, 6,663,820, 6,503,231, United States Patent Application 20100106105, and European Patent Application 2119469 A. For example, the microneedle array can be fabricated by wet etching processing or dry etching processing using a silicon substrate, precision machining using metal or resin (such as discharge machining, laser machining, dicing processing, hot embossing, and injection molding), and mechanical cutting. With such processing method, the needle part and the support part are molded into one piece. Example of method of hollowing the needle part includes a method of performing secondary processing by using laser machining and the like after the needle part is being prepared. In some cases a microneedle of the disclosure can be a microneedle that is solid (not hollow). In some cases a microneedle of the disclosure can be etched to increase a surface area of the microneedle.

A plurality of methods of cell disruption may be required to render the biomarker accessible to the probe. The cells can be disrupted by either disrupting the extracellular matrix, or disrupting the cell membrane. A device of the disclosure can cause cell disruption when, for example, at least one microneedle contacts and perforates a biological sample, such as a human skin.

A plurality of cells in situ or ex vivo can be disrupted with a substance. As such, the invention further provides a composition comprising a plurality of microneedles coated with a substance capable of disrupting an extracellular matrix. In some cases, the substance is an enzyme. A number of enzymes, including but not limited to serine proteases, thiol proteases, and MMPs, could be useful in this process. Non-limiting examples of enzymes that can be used for cell and tissue disruption include but are not limited to papain, hyaluronidase, streptokinase, streptodornase, trypsin, chymotrypsin, alpha-chymotrypsin, alpha-amlyase, DNase, collagenase, sutilain proteases, lysozyme, lipases, zymolase, cellulase, mutanolysin, or glycanases. In some examples, the enzyme is hyalurodinase.

Additional methods of cell and tissue disruption can include, for example, sonication, electroporation, cryopulverization, physical disruption with pressure, grinding, detergent-based cell lysis, or mechanical shearing of the tissue, with for example, a homogeneizer. For example, the extracellular matrix or cell membrane may be disrupted by an ultrasonic energy or by an electrical potential. Application of a solvent to a biological sample may also be used to render a biomarker available for hybridization with a probe.

A device of the disclosure may disrupt a biological tissue in situ or ex vivo in a minimally-invasive manner. For example, a microneedle of the disclosure can be contacted with the skin in the eye of a subject. The microneedle can gently disrupt the membrane of a layer of cells in the skin of the eye thereby providing access of a biomarker in the eye to a probe(s) in the microneedle. In some embodiments, the methods and devices of the disclosure can be applied to the identification and characterization of biomarkers from delicate tissues or inoperable tissues. For example biomarkers present in the eye or brain. In some embodiments, the methods and devices of the disclosure are applied to the in situ characterization of biomarkers from a biological sample that may not be available for surgical removal in a biopsy, for example, certain types of brain tumors.

Probe Conjugation and Assays for Amplifying and Detecting Biomarkers.

Microneedles Conjugated with Probes.

A plurality of probes can be attached to a microneedle of the disclosure. In some cases, the probes comprise polynucleotides (e.g., DNA, RNA, cDNA, cRNA, etc.). Often the polynucleotide probes are designed to bind or hybridize a specific polynucleotide biomarker. This disclosure also provides methods and devices for detecting peptide or protein biomarkers. In these embodiments, the probes attached to the microneedles can specifically recognize and bind to target peptides or proteins of interest. The probes can be any substance capable of binding to a specific peptide or protein biomarker. They can be, e.g., a protein (e.g., an antibody, antigen, or fragment thereof), carbohydrate, or a polynucleotide. The polynucleotide may possess sequence specificity for the biomarker.

The probes to be used depend on the biomarker or biomarkers to be detected. Thus, depending the nature and number of biomarkers to be detected, the number of probes immobilized to the microneedles can be 2, 3, 4, 5, 6, 7, 8, 9, 10, or more. In some cases, the total number of probes in a microneedle can be from about 1 probe to about 1,000 probes, from about 1 probe to about 10,000 probes, from about 1 probe to about 100,000 probes, from about 1 probe to about 1,000,000 probes, from about 1 probe to about 10,000,000, from about 1 probe to about 100,000,000 probes, from about 1,000 probes to about 10,000 probes, from about 1,000 probes to about 100,000 probes, from about 1,000 probes to about 1,000,000 probes, from about 1,000 probes to about 10,000,000, from about 1,000 probes to about 100,000,000 probes, from about 10,000 probes to about 100,000 probes, from about 10,000 probes to about 1,000,000 probes, from about 10,000 probes to about 10,000,000, from about 10,000 probes to about 100,000,000 probes, from about 100,000 probes to about 1,000,000 probes, from about 100,000 probes to about 10,000,000, from about 100,000 probes to about 100,000,000 probes, from about 1,000,000 probes to about 10,000,000, from about 1,000,000 probes to about 100,000,000 probes, or from about 10,000,000 probes to about 100,000,000 probes.

In some cases, the total number of probes in a microneedle is at least about 1, about 2, about 3, about 4, about 5, about 6, about 7, about 8, about 9, about 10, about 12, about 14, about 16, about 18, about 20, about 25, about 30, about 35, about 40, about 45, about 50, about 60, about 70, about 80, about 90, about 100, about 150, about 200, about 250, about 300, about 350, about 400, about 450, about 500, about 600, about 700, about 800, about 900, about 1000, about 1100, about 1200, about 1300, about 1400, about 1500, about 2000, about 2500, about 3000, about 3500, about 4000, about 4500, about 5000, about 6000, about 7000, about 8000, about 9000, about 10000, about 12000, about 14000, about 16000, about 18000, about 20000, about 30000, about 40000, about 50000, about 60000, about 70000, about 80000, about 90000, about 100000, about 200000, about 300000, about 400000, about 500000, about 600000, about 700000, about 800000, about 900000, about 1,000,000, about 2,000,000, about 3,000,000, about 4,000,000, about 5,000,000, about 6,000,000, about 7,000,000, about 8,000,000, about 9,000,000, about 10,000,000, about 20,000,000, about 30,000,000, about 40,000,000, about 50,000,000, about 60,000,000, about 70,000,000, about 80,000,000, about 90,000,000, or about 100,000,000 probes.

In some cases, the total number of probes in a microneedle is less than about 1, about 2, about 3, about 4, about 5, about 6, about 7, about 8, about 9, about 10, about 12, about 14, about 16, about 18, about 20, about 25, about 30, about 35, about 40, about 45, about 50, about 60, about 70, about 80, about 90, about 100, about 150, about 200, about 250, about 300, about 350, about 400, about 450, about 500, about 600, about 700, about 800, about 900, about 1000, about 1100, about 1200, about 1300, about 1400, about 1500, about 2000, about 2500, about 3000, about 3500, about 4000, about 4500, about 5000, about 6000, about 7000, about 8000, about 9000, about 10000, about 12000, about 14000, about 16000, about 18000, about 20000, about 30000, about 40000, about 50000, about 60000, about 70000, about 80000, about 90000, about 100000, about 200000, about 300000, about 400000, about 500000, about 600000, about 700000, about 800000, about 900000, about 1,000,000, about 2,000,000, about 3,000,000, about 4,000,000, about 5,000,000, about 6,000,000, about 7,000,000, about 8,000,000, about 9,000,000, about 10,000,000, about 20,000,000, about 30,000,000, about 40,000,000, about 50,000,000, about 60,000,000, about 70,000,000, about 80,000,000, about 90,000,000, or about 100,000,000 probes.

In addition, a probe for the biomarker can be immobilized to multiple microneedles in the device of the disclosure, particularly for detection of a biomarker of low concentration, as described further herein. In some cases, a single microneedle comprises multiple different probes capable of binding or detecting the same biomarker. In some cases, a single microneedle comprises at least 2 different probes for the same biomarker, at least 3 different probes, at least 4 different probes, at least 5 different probes, at least 6 different probes, at least 7 different probes, at least 8 different probes, at least 9 different probes, at least 10 different probes, at least 11 different probes, at least 12 different probes, at least 13 different probes, at least 14 different probes, at least 15 different probes, at least 16 different probes, at least 17 different probes, at least 18 different probes, at least 19 different probes, at least 20 different probes, at least 21 different probes, at least 22 different probes, at least 23 different probes, at least 24 different probes, at least 25 different probes, at least 26 different probes, at least 27 different probes, at least 28 different probes, at least 29 different probes, at least 30 different probes, at least 40 different probes, at least 41 different probes, at least 42 different probes, at least 43 different probes, at least 44 different probes, at least 45 different probes, at least 46 different probes, at least 47 different probes, at least 48 different probes, at least 49 different probes, or at least 50 different probes for the same biomarker. In some cases, the same microneedle comprises more than 50 different types of probes for the same biomarker.

In some cases, the same microneedle comprises a plurality of different probes. The different probes can be specific for the same biomarker or for a different biomarker. A microneedle can comprise at least 2 different probes, at least 10 different probes, at least 100 different probes, at least 200 different probes, at least 300 different probes, at least 400 different probes, at least 500 different probes, at least 600 different probes, at least 700 different probes, at least 800 different probes, at least 900 different probes, at least 1,000 different probes, at least 1,100 different probes, at least 1,200 different probes, at least 1,300 different probes, at least 1,400 different probes, at least 1,500 different probes, at least 1,600 different probes, at least 1,700 different probes, at least 1,800 different probes, at least 1,900 different probes, at least 2,000 different probes, at least 2,100 different probes, at least 2,200 different probes, at least 2,300 different probes, at least 2,400 different probes, at least 2,500 different probes, at least 2,600 different probes, at least 2,700 different probes, at least 2,800 different probes, at least 2,900 different probes, at least 3,000 different probes, at least 3,100 different probes, at least 3,200 different probes, at least 3,300 different probes, at least 3,400 different probes, at least 3,500 different probes, at least 3,600 different probes, at least 3,700 different probes, at least 3,800 different probes, at least 3,900 different probes, at least 4,000 different probes, at least 4,100 different probes, at least 4,200 different probes, at least 4,300 different probes, at least 4,400 different probes, at least 4,500 different probes, at least 4,600 different probes, at least 4,700 different probes, at least 4,800 different probes, at least 4,900 different probes, at least 5,000 different probes, at least 5,100 different probes, at least 5,200 different probes, at least 5,300 different probes, at least 5,400 different probes, at least 5,500 different probes, at least 5,600 different probes, at least 5,700 different probes, at least 5,800 different probes, at least 5,900 different probes, at least 6,000 different probes, at least 6,100 different probes, at least 6,200 different probes, at least 6,300 different probes, at least 6,400 different probes, at least 6,500 different probes, at least 6,600 different probes, at least 6,700 different probes, at least 6,800 different probes, at least 6,900 different probes, at least 7,000 different probes, at least 7,100 different probes, at least 7,200 different probes, at least 7,300 different probes, at least 7,400 different probes, at least 7,500 different probes, at least 7,600 different probes, at least 7,700 different probes, at least 7,800 different probes, at least 7,900 different probes, at least 8,000 different probes, at least 8,100 different probes, at least 8,200 different probes, at least 8,300 different probes, at least 8,400 different probes, at least 8,500 different probes, at least 8,600 different probes, at least 8,700 different probes, at least 8,800 different probes, at least 8,900 different probes, at least 9,000 different probes, at least 9,100 different probes, at least 9,200 different probes, at least 9,300 different probes, at least 9,400 different probes, at least 9,500 different probes, at least 9,600 different probes, at least 9,700 different probes, at least 9,800 different probes, at least 9,900 different probes, or at least 10,000 different probes. A microneedle can comprise less than 2 different probes, less than 10 different probes, less than 100 different probes, less than 200 different probes, less than 300 different probes, less than 400 different probes, less than 500 different probes, less than 600 different probes, less than 700 different probes, less than 800 different probes, less than 900 different probes, less than 1,000 different probes, less than 1,100 different probes, less than 1,200 different probes, less than 1,300 different probes, less than 1,400 different probes, less than 1,500 different probes, less than 1,600 different probes, less than 1,700 different probes, less than 1,800 different probes, less than 1,900 different probes, less than 2,000 different probes, less than 2,100 different probes, less than 2,200 different probes, less than 2,300 different probes, less than 2,400 different probes, less than 2,500 different probes, less than 2,600 different probes, less than 2,700 different probes, less than 2,800 different probes, less than 2,900 different probes, less than 3,000 different probes, less than 3,100 different probes, less than 3,200 different probes, less than 3,300 different probes, less than 3,400 different probes, less than 3,500 different probes, less than 3,600 different probes, less than 3,700 different probes, less than 3,800 different probes, less than 3,900 different probes, less than 4,000 different probes, less than 4,100 different probes, less than 4,200 different probes, less than 4,300 different probes, less than 4,400 different probes, less than 4,500 different probes, less than 4,600 different probes, less than 4,700 different probes, less than 4,800 different probes, less than 4,900 different probes, less than 5,000 different probes, less than 5,100 different probes, less than 5,200 different probes, less than 5,300 different probes, less than 5,400 different probes, less than 5,500 different probes, less than 5,600 different probes, less than 5,700 different probes, less than 5,800 different probes, less than 5,900 different probes, less than 6,000 different probes, less than 6,100 different probes, less than 6,200 different probes, less than 6,300 different probes, less than 6,400 different probes, less than 6,500 different probes, less than 6,600 different probes, less than 6,700 different probes, less than 6,800 different probes, less than 6,900 different probes, less than 7,000 different probes, less than 7,100 different probes, less than 7,200 different probes, less than 7,300 different probes, less than 7,400 different probes, less than 7,500 different probes, less than 7,600 different probes, less than 7,700 different probes, less than 7,800 different probes, less than 7,900 different probes, less than 8,000 different probes, less than 8,100 different probes, less than 8,200 different probes, less than 8,300 different probes, less than 8,400 different probes, less than 8,500 different probes, less than 8,600 different probes, less than 8,700 different probes, less than 8,800 different probes, less than 8,900 different probes, less than 9,000 different probes, less than 9,100 different probes, less than 9,200 different probes, less than 9,300 different probes, less than 9,400 different probes, less than 9,500 different probes, less than 9,600 different probes, less than 9,700 different probes, less than 9,800 different probes, less than 9,900 different probes, or less than 10,000 different probes.

In some cases, the plurality of probes are identical (e.g., identical copies of the same polynucleotide or antibody). In some embodiments, a microneedle can be associated with numerous copies of the same probe (e.g., greater than 2, 5, 10, 50, 100, 1000, 5000, 7500, 10000, or 50000 copies of the same probe). For example, a microneedle can comprise a plurality of copies of a polynucleotide probe designed to hybridize the same polymorphism or biomarker. In some cases, a microneedle may comprise a plurality of copies of an antibody probe designed to bind the same epitope.

In some cases, a microneedle comprises polynucleotide probes. The probes may be designed to detect different biomarkers associated with the same disease, disorder or condition. In some cases, a first probe recognizes a polymorphism (e.g., DNA polymorphism, RNA polymorphism) associated with a disease and a second probe recognizes a different polymorphism associated with the same disease. For example, a first DNA probe on a microneedle can be designed to detect a first polymorphism of an RNA biomarker associated with onchocerciasis, a skin condition. A second DNA probe on a microneedle can be designed to detect a second polymorphism of an RNA biomarker associated with onchocerciasis. A polymorphism can be, for example, a single nucleotide polymorphism (SNP). Genetic and genomic variations can comprise a single SNP or a plurality of SNPs. SNPs can occur at a single locus, or at many loci. Individuals who carry a particular SNP allele at one locus can predictably carry specific SNP alleles at other loci. A correlation of SNPs can provide an association between alleles predisposing an individual to disease or condition. In some cases, the different polynucleotide probes are designed to detect different biomarkers associated with different conditions. For example, one probe may detect a biomarker of a disease, while the other probe may detect a housekeeping gene or gene product. In some cases, the microneedles are attached to polynucleotides, polypeptides, or a mixture of polynucleotides and polypeptides.

A microneedle can also be associated with a plurality of different protein or antibody probes. For example, a first antibody probe on a microneedle can be designed to detect a first epitope of an antigen associated with, for example, a skin cancer. A second antibody probe can be designed to detect a second epitope associated with the antigen. Or, in some cases, the second antibody probe can detect an epitope associated with a different skin condition.

In some cases, this disclosure provides a microneedle device comprising a set of microneedles, wherein each microneedle in the set comprises identical probes or set of probes. In some embodiments, an identical probe is attached to a plurality of microneedles of a device. An identical probe can be attached to, for example, about 1% of the microneedles, about 5% of the microneedles, about 10% of the microneedles, about 15% of the microneedles, about 20% of the microneedles, about 25% of the microneedles, about 30% of the microneedles, about 35% of the microneedles, about 40% of the microneedles, about 45% of the microneedles, about 50% of the microneedles, about 55% of the microneedles, about 60% of the microneedles, about 65% of the microneedles, about 70% of the microneedles, about 75% of the microneedles, about 80% of the microneedles, about 85% of the microneedles, about 90% of the microneedles, about 95% of the microneedles, or about 100% of the microneedles. In some embodiments, an identical probe is attached to no greater than 5% of the microneedles, no greater than 10% of the microneedles, no greater than 15% of the microneedles, no greater than 20% of the microneedles, no greater than 25% of the microneedles, no greater than 30% of the microneedles, no greater than 35% of the microneedles, no greater than 40% of the microneedles, no greater than 45% of the microneedles, no greater than 50% of the microneedles, no greater than 55% of the microneedles, no greater than 60% of the microneedles, no greater than 70% of the microneedles, no greater than 75% of the microneedles, no greater than 80% of the microneedles, no greater than 85% of the microneedles, no greater than 90% of the microneedles, no greater than 95% of the microneedles, or no greater than 99% of the microneedles.

In some cases, a set of microneedles may comprise at least one microneedle attached to a first probe and at least one microneedle attached to a second probe that is different from the first probe. For example, as described herein, the first probe may be a polynucleotide or polypeptide (e.g., antibody, protein) that specifically binds a biomarker of a disease or disorder and the second probe may be a polynucleotide or polypeptide that specifically binds a different biomarker associated with the same disease or disorder. In some cases, the first probe may be a polynucleotide or polypeptide (e.g., antibody, protein) that specifically binds a biomarker of a disease or disorder and the second probe may be a polynucleotide or polypeptide that specifically binds a different biomarker associated with a different disease, disorder, or condition. In some cases, the different disease, condition, or disorder is associated with the same organ. For example, the first probe may be associated with a first disease, disorder, or condition associated with skin; and the second probe may be associated with a second disease, disorder, or condition associated with skin or eye. In some cases, the device may comprise an array of microneedles, wherein each microneedle comprises a probe that detects a biomarker associated with a different disease, disorder, or condition associated with the same organ. The array of microneedles may comprise greater than 2, 3, 4, 5, 6, 7, 8, 9, 10, 20, 30, 40, 50, 75, 100, 150, 200, 50, or 1000 microneedles associated with different diseases, disorders, or conditions. In some cases, the different diseases, disorders, or conditions are associated with different organs (e.g., greater than 1, 2, 3, 4, 5, 6, 7, 8, 9, 10, 15, or 20 organs).

In some cases, the microneedle device comprises a plurality of arrays of microneedles; often, the plurality of arrays of microneedles are suitable for multiplexed reactions. In some cases, the plurality of arrays comprises two or more arrays of microneedles, wherein the arrays are designed to detect a different biomarker. In some cases, a first array of microneedles may be designed to detect a biomarker associated with disease, disorder, or condition, and the second array of microneedles is designed to detect a different biomarker associated with the same disease, disorder, or condition. In some cases, a first array of microneedles may be designed to detect a biomarker associated with disease, disorder, or condition, and a second array of microneedles may be designed to detect a different biomarker associated with a different disease, disorder, or condition. In some cases, a first array of microneedles may be designed to detect a plurality of biomarkers associated with a disease, disorder, or condition; and a second array of microneedles may be designed to detect a plurality of biomarkers associated with a different disease, disorder, or condition. In some cases, the second array of microneedles may be designed to detect control biomarkers (e.g., housekeeping genes), either positive controls or negative controls.

In some cases, the methods and devices provided herein can be used to perform multiplex reactions with or without using fluorescence. For example, each microneedle can be inserted into its own cavity (e.g., pinprick cavity), containing unique PCR reagents (e.g., unique probes or primers). PCR reactions can be conducted and the samples can be analyzed for various biomarkers. In some cases, the multiplex reactions are performed with fluorescently-labeled probes, or probes that emit a different optical signal. In some cases, no fluorescence is used.

A microneedle device described herein may comprise any number of probes; often, the probes are attached to multiple needles within the device. The probes may be identical or different. In addition, a probe for the biomarker can be immobilized to multiple microneedles in the device of the disclosure, particularly for detection of a biomarker of low concentration. In some cases, the total number of probes in a microneedle device can be from about 1 probe to about 1,000 probes, from about 1 probe to about 10,000 probes, from about 1 probe to about 100,000 probes, from about 1 probe to about 1,000,000 probes, from about 1 probe to about 10,000,000, from about 1 probe to about 100,000,000 probes, from about 1,000 probes to about 10,000 probes, from about 1,000 probes to about 100,000 probes, from about 1,000 probes to about 1,000,000 probes, from about 1,000 probes to about 10,000,000, from about 1,000 probes to about 100,000,000 probes, from about 10,000 probes to about 100,000 probes, from about 10,000 probes to about 1,000,000 probes, from about 10,000 probes to about 10,000,000, from about 10,000 probes to about 100,000,000 probes, from about 100,000 probes to about 1,000,000 probes, from about 100,000 probes to about 10,000,000, from about 100,000 probes to about 100,000,000 probes, from about 1,000,000 probes to about 10,000,000, from about 1,000,000 probes to about 100,000,000 probes, or from about 10,000,000 probes to about 100,000,000 probes.

In some cases, the total number of probes in a microneedle device is at least about 1, about 2, about 3, about 4, about 5, about 6, about 7, about 8, about 9, about 10, about 12, about 14, about 16, about 18, about 20, about 25, about 30, about 35, about 40, about 45, about 50, about 60, about 70, about 80, about 90, about 100, about 150, about 200, about 250, about 300, about 350, about 400, about 450, about 500, about 600, about 700, about 800, about 900, about 1000, about 1100, about 1200, about 1300, about 1400, about 1500, about 2000, about 2500, about 3000, about 3500, about 4000, about 4500, about 5000, about 6000, about 7000, about 8000, about 9000, about 10000, about 12000, about 14000, about 16000, about 18000, about 20000, about 30000, about 40000, about 50000, about 60000, about 70000, about 80000, about 90000, about 100000, about 200000, about 300000, about 400000, about 500000, about 600000, about 700000, about 800000, about 900000, about 1,000,000, about 2,000,000, about 3,000,000, about 4,000,000, about 5,000,000, about 6,000,000, about 7,000,000, about 8,000,000, about 9,000,000, about 10,000,000, about 20,000,000, about 30,000,000, about 40,000,000, about 50,000,000, about 60,000,000, about 70,000,000, about 80,000,000, about 90,000,000, or about 100,000,000 probes.

In some cases, the total number of probes in a microneedle device is less than about 1, about 2, about 3, about 4, about 5, about 6, about 7, about 8, about 9, about 10, about 12, about 14, about 16, about 18, about 20, about 25, about 30, about 35, about 40, about 45, about 50, about 60, about 70, about 80, about 90, about 100, about 150, about 200, about 250, about 300, about 350, about 400, about 450, about 500, about 600, about 700, about 800, about 900, about 1000, about 1100, about 1200, about 1300, about 1400, about 1500, about 2000, about 2500, about 3000, about 3500, about 4000, about 4500, about 5000, about 6000, about 7000, about 8000, about 9000, about 10000, about 12000, about 14000, about 16000, about 18000, about 20000, about 30000, about 40000, about 50000, about 60000, about 70000, about 80000, about 90000, about 100000, about 200000, about 300000, about 400000, about 500000, about 600000, about 700000, about 800000, about 900000, about 1,000,000, about 2,000,000, about 3,000,000, about 4,000,000, about 5,000,000, about 6,000,000, about 7,000,000, about 8,000,000, about 9,000,000, about 10,000,000, about 20,000,000, about 30,000,000, about 40,000,000, about 50,000,000, about 60,000,000, about 70,000,000, about 80,000,000, about 90,000,000, or about 100,000,000 probes.

In some cases, a microneedle device comprises at least 2 different probes for the same biomarker, at least 3 different probes, at least 4 different probes, at least 5 different probes, at least 6 different probes, at least 7 different probes, at least 8 different probes, at least 9 different probes, at least 10 different probes, at least 11 different probes, at least 12 different probes, at least 13 different probes, at least 14 different probes, at least 15 different probes, at least 16 different probes, at least 17 different probes, at least 18 different probes, at least 19 different probes, at least 20 different probes, at least 21 different probes, at least 22 different probes, at least 23 different probes, at least 24 different probes, at least 25 different probes, at least 26 different probes, at least 27 different probes, at least 28 different probes, at least 29 different probes, at least 30 different probes, at least 40 different probes, at least 41 different probes, at least 42 different probes, at least 43 different probes, at least 44 different probes, at least 45 different probes, at least 46 different probes, at least 47 different probes, at least 48 different probes, at least 49 different probes, or at 50 different least probes for the same biomarker. In some cases, the same microneedle comprises more than 50 different types of probes for the same biomarker.

In some cases, a microneedle device comprises a plurality of different probes. The different probes can be specific for the same biomarker or for a different biomarker. A microneedle device can comprise at least 2 different probes, at least 10 different probes, at least 100 different probes, at least 200 different probes, at least 300 different probes, at least 400 different probes, at least 500 different probes, at least 600 different probes, at least 700 different probes, at least 800 different probes, at least 900 different probes, at least 1,000 different probes, at least 1,100 different probes, at least 1,200 different probes, at least 1,300 different probes, at least 1,400 different probes, at least 1,500 different probes, at least 1,600 different probes, at least 1,700 different probes, at least 1,800 different probes, at least 1,900 different probes, at least 2,000 different probes, at least 2,100 different probes, at least 2,200 different probes, at least 2,300 different probes, at least 2,400 different probes, at least 2,500 different probes, at least 2,600 different probes, at least 2,700 different probes, at least 2,800 different probes, at least 2,900 different probes, at least 3,000 different probes, at least 3,100 different probes, at least 3,200 different probes, at least 3,300 different probes, at least 3,400 different probes, at least 3,500 different probes, at least 3,600 different probes, at least 3,700 different probes, at least 3,800 different probes, at least 3,900 different probes, at least 4,000 different probes, at least 4,100 different probes, at least 4,200 different probes, at least 4,300 different probes, at least 4,400 different probes, at least 4,500 different probes, at least 4,600 different probes, at least 4,700 different probes, at least 4,800 different probes, at least 4,900 different probes, at least 5,000 different probes, at least 5,100 different probes, at least 5,200 different probes, at least 5,300 different probes, at least 5,400 different probes, at least 5,500 different probes, at least 5,600 different probes, at least 5,700 different probes, at least 5,800 different probes, at least 5,900 different probes, at least 6,000 different probes, at least 6,100 different probes, at least 6,200 different probes, at least 6,300 different probes, at least 6,400 different probes, at least 6,500 different probes, at least 6,600 different probes, at least 6,700 different probes, at least 6,800 different probes, at least 6,900 different probes, at least 7,000 different probes, at least 7,100 different probes, at least 7,200 different probes, at least 7,300 different probes, at least 7,400 different probes, at least 7,500 different probes, at least 7,600 different probes, at least 7,700 different probes, at least 7,800 different probes, at least 7,900 different probes, at least 8,000 different probes, at least 8,100 different probes, at least 8,200 different probes, at least 8,300 different probes, at least 8,400 different probes, at least 8,500 different probes, at least 8,600 different probes, at least 8,700 different probes, at least 8,800 different probes, at least 8,900 different probes, at least 9,000 different probes, at least 9,100 different probes, at least 9,200 different probes, at least 9,300 different probes, at least 9,400 different probes, at least 9,500 different probes, at least 9,600 different probes, at least 9,700 different probes, at least 9,800 different probes, at least 9,900 different probes, or at least 10,000 different probes. In some cases, a microneedle device can comprise less than 2 different probes, less than 10 different probes, less than 100 different probes, less than 200 different probes, less than 300 different probes, less than 400 different probes, less than 500 different probes, less than 600 different probes, less than 700 different probes, less than 800 different probes, less than 900 different probes, less than 1,000 different probes, less than 1,100 different probes, less than 1,200 different probes, less than 1,300 different probes, less than 1,400 different probes, less than 1,500 different probes, less than 1,600 different probes, less than 1,700 different probes, less than 1,800 different probes, less than 1,900 different probes, less than 2,000 different probes, less than 2,100 different probes, less than 2,200 different probes, less than 2,300 different probes, less than 2,400 different probes, less than 2,500 different probes, less than 2,600 different probes, less than 2,700 different probes, less than 2,800 different probes, less than 2,900 different probes, less than 3,000 different probes, less than 3,100 different probes, less than 3,200 different probes, less than 3,300 different probes, less than 3,400 different probes, less than 3,500 different probes, less than 3,600 different probes, less than 3,700 different probes, less than 3,800 different probes, less than 3,900 different probes, less than 4,000 different probes, less than 4,100 different probes, less than 4,200 different probes, less than 4,300 different probes, less than 4,400 different probes, less than 4,500 different probes, less than 4,600 different probes, less than 4,700 different probes, less than 4,800 different probes, less than 4,900 different probes, less than 5,000 different probes, less than 5,100 different probes, less than 5,200 different probes, less than 5,300 different probes, less than 5,400 different probes, less than 5,500 different probes, less than 5,600 different probes, less than 5,700 different probes, less than 5,800 different probes, less than 5,900 different probes, less than 6,000 different probes, less than 6,100 different probes, less than 6,200 different probes, less than 6,300 different probes, less than 6,400 different probes, less than 6,500 different probes, less than 6,600 different probes, less than 6,700 different probes, less than 6,800 different probes, less than 6,900 different probes, less than 7,000 different probes, less than 7,100 different probes, less than 7,200 different probes, less than 7,300 different probes, less than 7,400 different probes, less than 7,500 different probes, less than 7,600 different probes, less than 7,700 different probes, less than 7,800 different probes, less than 7,900 different probes, less than 8,000 different probes, less than 8,100 different probes, less than 8,200 different probes, less than 8,300 different probes, less than 8,400 different probes, less than 8,500 different probes, less than 8,600 different probes, less than 8,700 different probes, less than 8,800 different probes, less than 8,900 different probes, less than 9,000 different probes, less than 9,100 different probes, less than 9,200 different probes, less than 9,300 different probes, less than 9,400 different probes, less than 9,500 different probes, less than 9,600 different probes, less than 9,700 different probes, less than 9,800 different probes, less than 9,900 different probes, or less than 10,000 different probes.

Probes for detecting various biological markers can be obtained commercially or synthesized in accordance with methods well known in the art. The probes can be designed according to any suitable methods. For example, computerized search program can be used to design nucleic acid probes specific for target biomarker sequences (e.g., mRNAs) with minimal cross hybridization and similar hybridization efficiency. Such exemplary programs include Oligo 5.0 (National Biosciences Inc.), Primer 3 (MIT), and Array Designer (Telechem International Inc.). The nucleotide probes used in the present methods can have any suitable length, e.g., from about 15 to about 100 nucleotides. For protein biomarkers, specific probes (antibodies) for detecting the biomarkers can also be readily generated or commercially obtained. The nucleotide probes or polypeptide probes used in the present methods can comprise a detectable label. Any suitable label can be used. For example, the detectable label can be detected by optical, magnetic, mechanic, spectroscopic, photochemical, biochemical, immunochemical, radioactive or enzymatic means. In some embodiments, the detectable label is a fluorescent or chemiluminescent label, such as GFP; a magnetic moiety; a protein, such as avidin, streptavidin; or a peptide tag, such as a histidine tag or a FLAG tag.

Immobilized probes are present on the surface of the microneedle devices described herein. The immobilized probes may bind covalently or noncovalently to the surface of the microneedles by methods known in the art or the specific linking methods described in the Examples herein. For example, the probes can be conjugated to the microneedles via, e.g., a biotin-avidin or biotin-streptavidin interaction, a Protein A interaction, a Protein G interaction, a goat anti-mouse Fc interaction, an amide bond, or through any other covalent or noncovalent interaction. The probes can be covalently attached to the microneedles with or without a suitable spacer element between probe and microneedle surface such as poly(ethylene glycol) (PEG). Methods routinely practiced in the art for immobilizing antibody probes or nucleotide probes can be readily employed and modified as appropriate in the practice of the invention. Such methods are described in the art, e.g., Mendoza et al., Biotechniques 27:778-786, 1999; Arenkov et al., Anal. Biochem. 278:123-131, 2000; Zhu et al., Nat. Genet. 26:283-289, 2000; MacBeath et al., Science 289: 1760-1763, 2000; Jyoung et al., Biosens. Bioelectron. 21:2315-2319, 2006; Lu et al., Anal. Chem. 67:83 87, 1995; Vijayendran et al., Anal. Chem. 73:471-480, 2001; Nakanishi et al., Anal. Chem. 68: 1695-1700, 1996; Rowe et al., Anal. Chem. 71:433-439, 1999; Day et al., Bichem. J. 278:735-740, 1991; Fodor et al., Science 251: 767-773, 1991; Schene et al., Science 270: 467-470, 1995; Lamture et al., Nucl. Acids Res. 22: 2121-2125, 1994; Guo et al., Nucl. Acids Res. 22: 5456-5465, 1994; and PCT publications WO00/22108, WO01/75447 and WO02/12891.

The probes can also be modified with a reactive moiety and attached to the gold coated surface of one or more microneedles. The reactive moiety can be a thiol group. In some cases, a mineral salt can be added. Examples of mineral salts include but are not limited to lithium salts, potassium salts, sodium salts, magnesium salts, and calcium salts, often with a halide counter ion. In some cases, the mineral salt is sodium chloride. The mineral salt may be present at a concentration preferably between about 0.1 M to 2.0 M, about 0.2 M to 2.0 M, about 0.2 M to 1.5 M or about 0.5 M to 1.5M. In some cases, the concentration of the mineral salt is less than about 0.1 M, less than about 0.2 M, less than about 0.2 M, less than about 0.3 M, less than about 0.4 M, less than about 0.5 M, less than about 1.0 M, less than about 1.1 M, less than about 1.2 M, less than about 1.3 M, less than about 1.4 M, less than about 1.5 M, less than about 1.6 M, less than about 1.7 M, less than about 1.8 M, less than about 1.9 M, less than about 2.0 M, less than about 2.5 M, less than about 3.0 M, less than about 3.5 M, less than about 4.0 M, or less than about 4.5 M. In some cases, the concentration of the mineral salt is greater than about 0.1 M, greater than about 0.2 M, greater than about 0.2 M, greater than about 0.3 M, greater than about 0.4 M, greater than about 0.5 M, greater than about 1.0 M, greater than about 1.1 M, greater than about 1.2 M, greater than about 1.3 M, greater than about 1.4 M, greater than about 1.5 M, greater than about 1.6 M, greater than about 1.7 M, greater than about 1.8 M, greater than about 1.9 M, greater than about 2.0 M, greater than about 2.5 M, greater than about 3.0 M, greater than about 3.5 M, greater than about 4.0 M, or greater than about 4.5 M Capturing Biomarkers.

A microneedle that is covalently or non-covalently attached to a probe can be inserted into a biological sample in situ, such as human skin, eye, intraoperative tissue, dermal capillaries, etc. A microneedle covalently attached to a probe can also be inserted into a biological sample ex vivo, such as tissue extracted during a biopsy. The probe can be allowed to hybridize or bind to a biomarker under physiological conditions of the biological sample for a specified period of time. A temperature range of from about 20 to about 40 degrees Celsius, atmospheric pressure of 1, pH of 6-8, glucose concentration of 1-20 mM, atmospheric oxygen concentration, and earth gravity can be examples of physiological conditions for most subjects. The probe can be allowed to hybridize or bind to the biological sample for at least 1 minute, at least 2 minutes, at least 3 minutes, at least 5 minutes, at least 10 minutes, at least 15 minutes, at least 20 minutes, at least 25 minutes, at least 30 minutes, at least 45 minutes, at least 1 hour, at least 2 hours, at least 3 hours, at least 5 hours, at least 10 hours, or at least 24 hours. In some embodiments, the probe can be allowed to hybridize to the biological sample for no more than 1 minute, no more than 2 minutes, no more than 3 minutes, no more than 5 minutes, no more than 10 minutes, no more than 15 minutes, no more than 20 minutes, no more than 25 minutes, no more than 30 minutes, no more than 1 hour, no more than 2 hours, no more than 3 hours, nor more than 5 hours, or no more than 10 hours. A microneedle with a covalently or non-covalently linked probe can be removed from the biological sample, for example, the human skin. A biomarker that is hybridized or bound to a probe can be isolated from a biological sample by removing the microneedle from the human skin.

Detecting Biomarkers.

Some embodiments of the invention are directed to detecting polynucleotide biomarkers (e.g., mRNAs, DNA). In these embodiments, the probes (e.g., oligonucleotide probes, polynucleotide probes) for one or more specific biomarkers can be readily synthesized based on the sequences of the target biomarkers. Once nucleic acid biomarkers are bound to the probes on the microneedle device of the invention, they are typically subjected to an amplification reaction (e.g., PCR, reverse transcription PCR) or are detected by a labeled tag. The labeled tag may be directly linked to the probe that is attached to the microneedle or, in some cases, the labeled tag binds to the biomarker after it has already been captured by the probe attached to the microneedle.

Many methods routinely practiced in the art can be readily employed to amplify nucleic acid biomarkers obtained from a subject. These include, e.g., polymerase chain reaction (PCR) or reverse transcription PCR. See generally PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202 (each of which is incorporated by reference for all purposes). Other suitable amplification methods include the ligase chain reaction (LCR) (see Wu and Wallace, Genomics 4, 560 (1989), Landegren et al., Science 241, 1077 (1988), transcription amplification (Kwoh et al., Proc. Natl. Acad. Sci. USA 86, 1173 (1989)), and self-sustained sequence replication (Guatelli et al., Proc. Nat. Acad. Sci. USA, 87, 1874 (1990)) and nucleic acid based sequence amplification (NASBA). The latter two amplification methods involve isothermal reactions based on isothermal transcription, which produce both single stranded RNA (ssRNA) and double stranded DNA (dsDNA) as the amplification products in a ratio of about 30 or 100 to 1, respectively. Once amplified, identity of the captured biomarkers can be then readily confirmed by standard techniques, e.g., sequencing analysis, electrophoresis, etc.

Some embodiments of the invention use PCR to detect a biomarker that is hybridized, or otherwise connected to a probe. The amplification of a biomarker by PCR can be across several orders of magnitude, sometimes starting from a single or a few copies of the target and generating thousands to millions of copies of a particular DNA sequence. PCR can use thermal cycling, comprising cycles of repeated heating and cooling of the reaction for DNA melting and enzymatic replication of the DNA. These thermal cycling operations can physically separate the two strands in a DNA double helix at a high temperature in a process called DNA melting. At a lower temperature, each strand can then be used as the template in DNA synthesis by the DNA polymerase to selectively amplify the target DNA. The selectivity of PCR can result from the use of primers (short DNA fragments) that are complementary to the DNA region targeted for amplification under specific thermal cycling conditions.

Primers containing sequences complementary to a biomarker of interest along with a DNA polymerase can be used to achieve selective and repeated amplification. As PCR progresses, the DNA generated can be used as a template for replication, setting in motion a chain reaction in which the DNA template is exponentially amplified. PCR applications can employ a heat-stable DNA polymerase, such as Taq polymerase, an enzyme originally isolated from the bacterium *Thermus aquaticus*. This DNA polymerase can enzymatically assemble a new DNA strand from the nucleotides, e.g., by using single-stranded DNA as a template and DNA oligonucleotides (also called DNA primers) for initiation of DNA synthesis.

A PCR reaction can be performed directly on a microneedle that has been inserted into a biological sample. For example the microneedle may be placed in a tube or between two plates (e.g., glass slides) comprising the necessary reagents for a PCR reaction. A biomarker may be detached from the needle and released into the PCR tube by a plurality of different methods. For example, a microneedle may be heated to release the biomarker from the microneedle, or a biomarker may spontaneously be released from the needle into the PCR solution. A PCR reaction can be performed as described above and the PCR product can be analyzed using standard procedures, for example, electrophoresis, real-time PCR, and other procedures, such as described in PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990). Different PCR methods can be used to analyze the sample, such as standard PCR methods and Real-time PCR methods. Real-time PCR (RT-PCR) is a laboratory technique based on PCR, which can be used to amplify and simultaneously quantify a targeted DNA molecule. Real-time PCR can be combined with reverse transcription to quantify messenger RNA and non-coding RNA in cells or tissues.

In some embodiments, a device of the disclosure can be further configured to comprise at least one compartment that can perform a PCR reaction. For example, a device of the disclosure may be configured to comprise a plurality of microneedles or an array of microneedles and a compartment where a PCR reaction can be performed.

A PCR reaction can selectively amplify a biomarker that has been hybridized to a particular microneedle or a PCR reaction can amplify a set of biomarkers that have been hybridized to a plurality of microneedles. For example, 402 illustrates a surface of a device of the invention comprising a plurality of microneedles that have been contacted with a biological sample. Each "square" in 402 illustrates an individual microneedle, wherein each individual microneedle comprises at least one probe. Each probe in 402 can hybridize to a biomarker, or not. Each microneedle illustrated in 402 can be placed into a separate PCR tube and each PCR product can be analyzed individually. Alternatively, a plurality of microneedles illustrated in 402 can be placed into the same PCR tube for simultaneous analysis.

In some cases, a captured biomarker may be detected by using a labeled probe capable of binding to the captured biomarker. In some cases, the labeled probe binds to the biomarker after the biomarker has already been captured by a probe attached to a microneedle described herein. In some cases, the microneedle is directly attached to a probe that is tagged with a label designed to change its optical signal (either decreasing or increasing in intensity) when bound to a biomarker.

The labeled probe may comprise a label (e.g., fluorophore, radioisotope, etc.) that can emit an optical signal. A fluorescent moiety can be a fluorescent protein, such as a green fluorescent protein (GFP), read fluorescent protein (RFP), yellow fluorescent protein (YFP) or variations thereof. In some cases, the labeled probe comprises a label with an optical signal that increases or decreases when the probe is bound to its target. A fluorescent moiety can be an RNA aptamer that binds fluorophores. An RNA-fluorophore complex can emit an optical signal that spans the visible spectrum, see Paige et al, Science 333, 6042 (2011). For example, the "Spinach aptamer sequence" is an RNA mimic of GFP that can be configured to emit a fluorescent optical signal when hybridized to a biomarker.

In some embodiments, a microneedle comprising a set of probes that are not-covalently or covalently bound therein can be used to detect a biomarker in a subject. For example, a device of the disclosure can be contacted to the skin of a subject. The device can comprise a polynucleotide probe comprising an RNA-fluorophore moiety. The RNA-fluorophore moiety can be configured to emit an optical signal, such as a fluorescence signal, when hybridized to a biomarker of interest.

Protein or peptide biomarkers can be detected and quantified by any of a number of methods well known to those of skill in the art for polypeptide detection. These include assay formats such as protein PCR and ELISAs. Both local and systemic protein and peptide biomarkers can be assayed using the microneedle array devices of the invention. Other methods suitable for this purpose include analytic biochemical methods such as electrophoresis, capillary electrophoresis, high performance liquid chromatography (HPLC), thin layer chromatography (TLC), hyperdiffusion chromatography, mass spectroscopy and the like, or various other immunological methods such as fluid or gel precipitin reactions, immunodiffusion (single or double), immunohistochemistry, affinity chromatography, immunoelectrophoresis, radioimmunoassay (RIA), immunofluorescent assays, Western blotting, dipstick, and the like. For a general review of immunoassays, see also Methods in Cell Biology Volume 37: Antibodies in Cell Biology, Asai, ed. Academic Press, Inc. New York (1993); Basic and Clinical Immunology 7th Edition, Stites & Terr, eds. (1991); IMMUNOASSAYS FOR THE 80s. Voller, A. et al (editors), Baltimore: University Park Press (1981); Maggio, et al, ENZYME-IMMUNOASSAY, Boca Raton: CRC Press pp 172-176 (1980) and Tijssen, Laboratory Techniques in Biochemistry and Molecular Biology: Practice and Theory of Immunoassays, vol 15, Elsevier 1985. Reagents for performing these assays with respect to any specific protein or peptide biomarker (e.g., antibodies) can be readily obtained from commercial sources or generated by standard and routinely practiced techniques (e.g., hybridoma technology for producing monoclonal antibodies).

Binding interactions between a probe and a biomarker can be detected using a secondary detection reagent, such as a secondary antibody. For example, a "sandwich ELISA" can be used to detect binding of a biomarker to an antibody probe. The binding of a biomarker to a probe can be detected using a detection antibody that is specific to a different epitope of the biomarker. The antibody used in the detection can be of a different isotype than the antibody used as a probe, for example, an antibody probe can be an IgG antibody (including any of the subtypes, such as IgG1, IgG2, IgG3 and IgG4), and a secondary antibody can be of the IgA, IgM). The detection antibody can be, for example conjugated to a detectable label, such as a fluorescent moiety or a radioactive label. An antibody based method of detection, such as an enzyme-linked immunosorbent assay (ELISA) method can be used to detect a binding of a probe to a biomarker.

Protein and peptide biomarkers can also be assayed using protein PCR techniques. For example, one assay suitable for detecting the biomarkers in these applications is the PCR-ELISA protocol. The assay employs a standard immunoassay procedure. A capture antibody is attached to the surface of the microneedles of the devices. Instead of using a reporter enzyme for development of analytical signal, the secondary antibody is fused to a single stranded oligonucleotide that can then be amplified using PCR. After insertion and capture of the biomarkers, the presence of the biomarkers can be detected by addition of the oligonucleotide-labeled secondary antibody and subsequent PCR analysis of the conjugated tag.

Diagnostic Applications and Related Kits.

The devices and methods described herein are useful for detecting and capturing biomarkers in various diagnostic applications. These include, e.g., diagnosis of skin diseases, detection of circulating genetic markers, and detection of protein or peptide biomarkers. As an example, the devices can be readily employed in the diagnosis of cutaneous malignant melanoma (CMM) in subjects suspected to have or to be at risk of developing CMM. In these applications, probes for CMM-specific biomarkers can be coupled to microneedles. Devices containing one or more of the probe-conjugated microneedles can then be applied directly to all moles (nevi) on a subject's skin. The devices are removed from each nevus, and any biomarkers captured by the microneedles are then assayed either in situ on the device or after separation from the devices. A device of the disclosure can be used clinically for diagnostic and prognostic applications.

As another specific application, the devices and methods described herein are employed in margin detection during skin cancer resection surgery. In these embodiments, the devices contain probe-conjugated microneedles of different lengths. Detection and assaying of tumor specific biomarkers with these devices can inform the surgeon about the extent of tumor invasion in the cutaneous, subcutaneous and underlying space. These applications obviate the iterative histopathological examination that is currently required to determine margins during skin tumor resection. In some cases, the method does not comprise biopsy of the skin.

A method and a device of the invention can be used in the diagnosis and/or treatment of a skin conditions. These methods can comprise contacting the microneedle with the skin tissue of a subject. A skin condition can be a benign condition, a pre-malignant condition, or a malignant condition. A skin condition can be a healthy condition. Non-limiting examples of skin conditions include: skin cancer, such as melanoma and Mohs skin cancer; onchocerciasis; lupus; rubeola (measles); hemangioma; psoriasis; rosacea; seborrheic eczema; hives, vitiligo; warts; necrotizing fasciitis; cutaneous candidiasis; carbuncle; cellulitis; hypohidrosis; impetigo; cutis laxa; decubitus ulcer; erysipelas; dyshidrotic eczema; canker sore; mole(s); herpes stomatitis; ichthyosis vulgaris; acne; cold sore; dermatomyositis; molluscum contagiosum; acrodermatitis; sebaceous cyst; seborrheic keratosis; pilonidal sinus; keloid; lichen planus; actinic keratosis; stasis dermatitis; skin corns and calluses; eczema; tinea versicolor; pemphigoid; ulcers; or shingles. A method and a device of the invention can be used in the diagnosis and treatment of a plurality of ocular conditions such as uveitis, dry eye disease, retinal disease, glaucoma, inflammatory diseases. A device of the invention can be used to stage a cancer. A cancer can be staged as stage 0, stage I, stage II, stage III, or stage IV.

A method and a device of the invention can also be used in the diagnosis and/or treatment of an eye conditions, such as, for example, corneal surface inflammation, uveitis, or dry eye disease. These methods can comprise contacting the microneedle with the eye tissue of a subject, for example, by contacting the sub-conjunctival space. An eye condition can be a benign condition, a pre-malignant condition, or a malignant condition. A eye condition can be a healthy condition. Non-limiting examples of eye conditions include: retinoblastoma; cutaneous or intraocular (eye) melanoma; retinitis pigmentosa (RP); diabetic retinopathy; glaucoma, (including open-angle glaucoma (e. g., primary open-angle glaucoma), angle-closure glaucoma, and secondary glaucomas (e. g., pigmentary glaucoma, pseudoexfoliative glaucoma, and glaucomas resulting from trauma and inflammatory diseases)), retinal detachment, age-related or other maculopathies, age-related macular degeneration, photic retinopathies, surgery-induced retinopathies, toxic retinopathies, retinopathy of prematurity, retinopathies due to trauma or penetrating lesions of the eye, inherited retinal degenerations, surgery-induced retinopathies, toxic retinopathies, retinopathies due to trauma or penetrating lesions of the eye. Specific exemplary inherited conditions of interest include, but are not necessarily limited to, Bardet-Biedl syndrome; Congenital amaurosis; Cone or cone-rod dystrophy; Congenital stationary night blindness; Macular degeneration; Optic atrophy; Syndromic or systemic retinopathy; and Usher syndrome.

A method and a device of the invention may be used to monitor the expression of a biomarker in a surgical procedure or in a cosmetic procedure. The device and methods of the disclosure can be used to, for example perform a biopsy of delicate tissues, such as the eye tissue or brain tissue. In some cases, the microneedle device can be contacted with the tissue or biological sample of the subject during an intraoperative procedure. The tissue or biological sample can be obtained from an organ selected from the group consisting of brain, heart, breast, liver, pancreas, spleen, bladder, stomach, lung, uterus, cervix, prostate, kidney, intestine, appendix, and colon. In further cases, the microneedles can be contacted to the margins of a tumor before or after the tumor is removed from the subject.

As a further example of the diagnostic applications of the invention, the methods and devices described herein can be used in the detection of systemic and circulating genetic biomarkers in a bodily fluid (e.g., the blood stream) of a subject. Many diseases (e.g., Down's syndrome) are known to have genetic (e.g., mRNA) biomarkers that circulate in the blood. By extending the lengths of the microneedles in the devices of the invention, probes for the biomarkers are capable of specifically binding to such biomarkers by penetrating into and accessing dermal or subcutaneous capillaries. Any other nucleic acid biomarkers that are known to be present in the blood can also be detected in a similar manner. For example, the microneedles on a device of the disclosure can penetrate the skin of a subject in situ, and be in contact with the dermal capillaries of the subject. Dermal capillaries can be the smallest blood vessels in the body of a subject and the endothelial linings of dermal capillaries can be about one cell layer thick. A device of the disclosure can penetrate the membrane of one, or a plurality of dermal capillaries when the device is contacted to a skin of a subject. In some embodiments, a device of the disclosure may be utilized to test biomarkers circulating in the bloodstream without the removal of a blood sample from a subject. In some cases, a device of the disclosure can detect fetal or maternal biomarkers of a condition, including pregnancy associated biomarkers. In some cases, a device of the invention can detect biomarkers circulating in the bloodstream such as proteins, hormones, vitamins, co-factors, or polynucleotides.

Non-limiting examples of genetic conditions that can be diagnosed with a method and a device of the invention based on a polynucleotide biomarker include: cystic fibrosis; Duchenne muscular dystrophy; Haemochromatosis; Tay-Sachs disease; Prader-Willi syndrome; Angelman syndrome; neurofibromatosis; phenylketonuria; Canavan disease; Coeliac disease; Acid beta-glucosidase deficiency; Gaucher; Charcot-Marie-Tooth disease; color blindness; Cri du chat; polycystic kidney disease; acrocephaly; familial adenomatous polyposis; adrenal gland disorders; amyotrophic lateral sclerosis (ALS); Alzheimer's disease; Parkinson's disease; anemia; ataxia; ataxia telangiectasia; autism; bone marrow diseases; Bonnevie-Ullrich syndrome; brain diseases; von Hippel-Lindau disease; congenital heart disease; Crohn's disease; dementia; myotonic dystrophy; Fabry disease; fragile X syndrome; galactosemia; genetic emphysema; retinoblastoma; Pendred syndrome; Usher syndrome; Wilson disease; neuropathies; Huntington's disease; immune system disorders; gout; X-linked spinal-bulbar muscle atrophy; learning disabilities; Li-Fraumeni syndrome; lipase D deficiency; Lou Gehrig disease; Marfan syndrome; metabolic disorders; Niemann-Pick; Noonan syndrome; Osteopsathyrosis; Peutz-Jeghers syndrome; Pfeiffer syndrome; porphyria; progeria; Rett syndrome; tuberous sclerosis; speech and communication disorders; spinal muscular atrophy; Treacher Collins syndrome; trisomies; and monosomies.

In some cases, the probes of the invention can be used to detect a condition of the immune system. A device of the invention can be used in allergy testing to confirm or to rule out allergies. In some cases a device of the invention can be used to analyze an allergy panel. Non-limiting examples of immune disorders include: HIV, diabetes, Parkinson's disease, Alzheimer's, rheumatoid arthritis, lupus, cancer, multiple sclerosis, inflammatory bowel disease, psoriasis, scleroderma, autoimmune thyroid disease, vasculitis, pernicious anemia, severe combined immunodeficiency (SCID), DiGeorge syndrome, hyperimmunoglobulin E syndrome, common variable immunodeficiency, chronic granulomatous disease, Wiskott-Aldrich syndrome, autoimmune lymphoproliferative syndrome (ALPS), hyper IgM syndrome, leukocyte adhesion deficiency (LAD), NF-κB essential modifier (NEMO) disorders, selective immunoglobulin A deficiency, X-linked agammaglobulinemia, X-linked lymphoproliferative disease, ataxia-telangiectasia, seasonal allergy, mastocytosis, perennial allergy, anaphylaxis, food allergy, allergic rhinitis, and atopic dermatitis.

In some embodiments, the devices and methods of the invention can be used to diagnose a variety of biomarkers associated with a plurality of cancers. Non-limiting examples of cancers can include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell cancer, stomach cancer, T-cell lymphoma, throat cancer, thymoma, thymic carcinoma, thyroid cancer, trophoblastic tumor (gestational), cancers of unkown primary site, urethral cancer, uterine sarcoma, vaginal cancer, vulvar cancer, Waldenström macroglobulinemia, and Wilms tumor.

A device of the disclosure can be used for an independent diagnostic method, or as a companion diagnostic to inform a therapeutic treatment. The microneedle and methods of the disclosure provide a method of diagnosis and a method of treatment that is minimally-invasive, fast, and accurate. In addition, the devices and methods disclosed herein can provide a portable, pain-free, and affordable diagnosis to a plurality of subjects. A subject of the invention can be of any age, including, for example, elderly adults, adults, adolescents, pre-adolescents, children, toddlers, and infants. A subject of the invention can be a mammal, a bird, a fish, a reptile, or an amphibian. Non-limiting examples of a subject include humans, primates, dogs, cats, horses, pigs, and mice.

A subject can provide a plurality of biological samples for an analysis with a microneedle of the invention. An analysis of a biological sample of a subject can be performed in situ or ex vivo. For example, an in situ analysis can comprise contacting a microneedle of the invention directly to the skin of a subject. An ex vivo analysis can comprise contacting a microneedle of the invention to a biopsy tissue. In some embodiments, about 1 mg, about 5 mgs, about 10 mgs, about 15 mgs, about 20 mgs, about 25 mgs, about 30 mgs, about 35 mgs, about 40 mgs, about 45 mgs, about 50 mgs, about 55 mgs, about 60 mgs, about 65 mgs, about 7 mgs, about 75 mgs, about 80 mgs, about 85 mgs, about 90 mgs, about 95 mgs, or about 100 mgs of a biological sample are required for a biomarker analysis with a microneedle and method of the invention.

In some embodiments, no more than about 1 mg to about 5 mgs, no more than about 1 mg to about 10 mgs, no more than about 1 mg to about 20 mgs, no more than about 1 mg to about 30 mgs, no more than about 1 mg to about 40 mgs, no more than about 1 mg to about 50 mgs, no more than about 50 mgs to about 60 mgs, no more than about 50 mgs to about 70 mgs, no more than about 50 mgs to about 80 mgs, no more than about 50 mgs to about 90 mgs, no more than about 50 mgs to about 100 mgs, no more than about 100 mgs to about 1 gram, no more than about 100 mgs to about 2 grams, no more than about 100 mgs to about 3 grams, no more than about 100 mgs to about 4 grams, no more than about 100 mgs to about 5 grams, no more than about 100 mgs to about 6 grams, no more than about 100 mgs to about 7 grams, no more than about 100 mgs to about 8 grams, no more than about 100 mgs to about 9 grams, no more than about 100 mgs to about 10 grams, no more than about 1 gram to about 2 grams, no more than about 1 gram to about 3 grams, no more than about 1 gram to about 4 grams, no more than about 1 gram to about 5 grams, no more than about 1 gram to about 6 grams, no more than about 1 gram to about 7 grams, no more than about 1 gram to about 8 grams, no more than about 1 gram to about 9 grams, or no more than about 1 gram to about 10 grams of biological sample are required by the methods and microneedle of the invention.

In some embodiments, additional assays are used to validate a diagnosis that is made based on the identification of biomarker identified with a microneedle and a method of the disclosure. Non-limiting examples of assays that can validate a biomarker include: a) assays that evaluate the interactions of proteins with DNA, such as DNase footprinting assay and gel shift assays; b) assays that evaluate the integrity of an RNA molecule, such as nuclear run-on assays; c) end point assays, which can measure quantitatively or qualitatively the end result of an assay; d) kinetic assays, which can evaluate readings of data points at multiple time intervals and compare the kinetics of a biological process; e) semi-quantitative assays, which provide a readout that can be quantitated within a context, such as western-blots, clotting and agglutination assays; f) immunoassays, which evaluate the response of an antigen antibody binding type of reaction; g) enzyme activity assays, which test function and activity; h) colony forming assays, which can test the ability of a cell to proliferate and differentiate; i) counting assays, such as flow cytometry assays; and j) a plurality of PCR assays, such as real-time PCR.

Further, the methods of the disclosure can further comprise detecting one or more biomarkers from a reference tissue obtained from the subject. For example, the method may comprise detecting biomarkers from a sample tissue and a reference tissue. The reference tissue can be a benign tissue. In some cases, the reference tissue is tissue from the same organ or region as the sample tissue. In some cases, the sample tissue comprises tissue suspected to have a disease or disorder (e.g., malignancy) and the reference tissue comprises tissue of the same organ that is known to not have the disease or disorder. In some cases, the detected levels of the biomarker in the sample tissue can be further compared to the detected levels of the biomarker in the reference tissue.

In some cases, a device of the disclosure can be used during surgery to remove tumors and/or to identify tumor margins. A device of the invention can be used to characterize tissues and tissue margins with distinct morphologies in situ or ex vivo. For example, in Mohs skin cancer surgery, where tissue is usually removed, sectioned and evaluated by histological methods a device of the invention could be used to analyze the margins of the tumor. In some cases, a device of the invention can be used to identify the metastasis of a cancer by analyzing the margins of a tissue.

A device and methods of the disclosure can be utilized in personalized medicine applications. A subject can provide a quantity of, for example, a skin sample to a clinician. The clinician may use a device of the disclosure to test for a plurality of biomarkers associated with the skin of the subject. The clinician may use the identified biomarkers to determine the expected efficacy of a treatment on a particular subject. A device and a method of the disclosure may also be used to monitor the response of a subject to a particular treatment, for example, by monitoring an increase or a decrease in the expression of a biomarker. A clinician may rely on an increase or a decrease of a biomarker expression level to determine an effectiveness of a treatment. A device of the invention can be used to quantitatively measure the expression of a biomarker. For example, quantitative PCR can be used to amplify the number of copies of a biomarker that has hybridized to a polynucleotide probe on a microneedle. A microneedle that has not been contacted or hybridized with a biological sample can be used a negative control. A microneedle with a known amount of a standard control, such as a housekeeping gene, can be used as a positive control for the reaction. Quantitative PCR can be performed as described in The PCR Technique: Quantitative PCR, James W. Larrick, June 1997, Eaton Publishing.

A device and methods of the disclosure can be used in biodefense. Biodefense can comprise detecting the release or dissemination of biological or chemical agents. These agents can be bacteria, viruses, or toxins, and may be in a naturally occurring or a human-modified form. A device of the disclosure can be used to detect a plurality of biomarkers associated with pathological agents that can be used in a biological war.

An agent of biological and/or chemical warfare can include any biological and/or chemical entity that can be used as a weapon, e.g., to cause terror, chaos, disease, discomfort and/or death. Non-limiting examples of chemical and biological agents include anthrax; small pox; tularemia; avian flu; plague; HIV; ebola; foot and mouth disease; ricin; neurotoxic organophosphates; cyanide; vesicants (or blister agents) such as mustard gas and Lewisite; choking agents, such as chlorine and phosgene; nerve agents, such as sarin, Tabun, Soman, and VX; hallucinogens, such as BZ; pesticides such as parathion, malathion, and azinphosmethyl; and derivatives or combinations thereof.

The invention further provides kits for carrying out the diagnostic applications described herein. The kits typically contain a microneedle device comprising one or more microneedles. In some kits, the microneedles are already conjugated with probes specific for detecting one or more biomarkers. In some other kits, probes for detecting one or more biomarkers and reagents for their conjugation to the microneedles are provided as separate components. Some kits of the invention are intended for detecting and capturing one specific biomarker for a known disease or disorder (e.g., Plakophilin-3 mRNA for gastrointestinal cancer). In these kits, the microneedles of the device usually are conjugated or to be conjugated with the same probe molecule (e.g., an oligonucleotide complementary to the target biomarker). Some other kits of the invention are designed for detection of a plurality of biomarkers implicated in one or more diseases or disorders. In these kits, different probes for the different biomarkers are conjugated or provided for conjugation to the microneedles of the device. In addition to the microneedle device and probes, the kits of the invention can also include other reagents for applying the device to a subject and for analyzing the captured biomarker (e.g., reagents for PCR amplification of biomarkers). The kits can further contain instructions (e.g., on an instruction sheet in the kits or packaging material of the kits) for using the kits to carry out the intended diagnostic applications.

Devices of the invention can be packaged as a kit. In some embodiments, a kit includes written instructions on the use of the device for treatment of a condition, such as basal cell carcinoma. The written material can be, for example, a label. The written material can suggest conditions and methods of using the microneedle and additional reagents comprised in the kit. The instructions provide the subject and the supervising physician with the best guidance for achieving the optimal detection of a biomarker.

A kit of the disclosure may comprise a device described herein and a set of reagents for a polymerase chain reaction. A kit of the disclosure may comprise a device described herein and a set of reagents for an ELISA assay. A kit may be designed for the identification of a specific condition, such as basal cell carcinoma or a kit may be designed for the simultaneous diagnosis of a plurality of conditions, such as squamous cell carcinoma, Kaposi's sarcoma, melanoma, basal cell carcinoma, and actinic keratosis (a precursor to squamous cell carcinoma). In some cases, a kit of the disclosure may comprise a device of the invention and written material. In some cases, a kit of the disclosure may comprise a device of the invention, a set of probes, and a set of reagents that can be used to link the probes to the microneedles.

A kit of the disclosure can comprise positive and negative controls. A positive control can be, for example, a sample comprising a known biomarker. A positive control can be a polynucleotide of known sequence, such as a polynucleotide of a known SNP associated with basal cell carcinoma. A negative control can be, for example, a scrambled polynucleotide sequence. In some cases, the kit may comprise reagents (e.g., polypeptide, polynucleotide) of known concentrations or quantities that can be used to prepare a standard curve in order to quantify the amount of biomarker present in a tissue or biological sample. Such reagents may also be used in conjunction with any method provided herein.

Animal Models.

Many drugs, treatments, and cures for diseases can be developed with the use of animal models. An animal model can be a live animal used during the research and investigation of disease. The pharmaceutical development of a drug can include the investigation of toxic and adverse side effects that are not detected in cellular assays. An animal model can be used to appraise efficacy, absorption, metabolism, distribution, excretion, toxicity, pharmacology, and side effects of a pharmacological treatment. A device and the methods of the invention can be used to identify the response of a biomarker on an animal model to a pharmacological treatment.

An animal model can provide guidance for the selection of pharmacological compounds for further evaluation. An animal model can, for example, provide guidance for pharmacokinetic/metabolic studies in humans. An animal model can be used, for example, for the evaluation of absorption, distribution, metabolism, excretion, and toxicology (AD-MET) parameters supporting an Investigational New Drug (IND) application. Studies in an animal model can, for example, lead to the selection of compounds to be further evaluated in pre-clinical and clinical trials.

Clinical Intervention and Clinical Trials

A device of the disclosure can be used in a clinical trial. For example, a device of the disclosure may be used during a surgical procedure to identify a biomarker in a tissue that is difficult to reach, or a tissue that cannot be excised and removed for a biopsy. For example, a device of the disclosure can be applied to the detection of a biomarker in a cardiovascular tissue, a brain tissue, or an internal organ that is exposed to a clinician during a surgical procedure. In some cases, a device of the invention can prevent medical complications that otherwise can arise when a clinician removes tissue from a subject for a biopsy. A device of the disclosure can be used, for example, in a routine medical consultation, during a surgical procedure, or by a subject at a subject's home. A device of the invention can be used, for example, in cardiovascular surgery or eye surgery.

A device of the disclosure can be used in the design of a clinical trial protocol. For example, a device of the disclosure can be used in conjunction with a clinical trial to detect the levels of a biomarker and to monitor the response of a subject to a pharmacological treatment. A device of the disclosure can provide guidelines for the design, conduct, and analyses of pre-clinical development and clinical trials. The disclosure provides a method of identifying and quantifying biomarkers that can be selected for the optimal administration of therapeutically effective compounds.

A device of the disclosure can be used in predicting the subject's response to distinct drug dosages in a clinical trial. For example, by monitoring increases or decreases in the levels of a biomarker, such as a biomarker of retinal disease, in an ocular tissue the methods and devices of the invention can establish an efficacy of a pharmacological treatment for the retinal disease. In some cases, a clinical trial for a therapeutic agent is conducted or altered based on the detection of a biomarker with a device of the disclosure. In some cases, the methods and devices of the disclosure can be used to compare a treatment being evaluated in a clinical trial to a known standard-of-care treatment.

Clinical trials typically proceed through several steps, including pre-clinical studies, pilot studies, safety screening studies, and efficacy evaluation studies. For a drug to be approved and marketed, all milestones specified in a clinical trial protocol must often be met, including, demonstration of efficacy within a proposed confidence interval, and inclusion of a significant number of individuals to demonstrate the statistical power of the invention. Non-limiting examples of applications of the invention include the monitoring of a plurality of biomarkers throughout the course of a clinical trial. A device and methods of the disclosure can also be used to monitor how distinct pharmacological treatments can affect the expression of biomarkers in the early stages of a clinical trial (pre-clinical and phase I).

A device and a method of the disclosure can also be used to predict changes in underlying cellular pathways affected by a pharmacological treatment based on the expression levels of the identified biomarkers. Non-limiting examples of pharmacodynamic and pharmacokinetic parameters of a pharmacological treatment that can affect an underlying cellular pathway include: a) the amount of drug administered, which can be represented as a dose D; b) the dosing interval, which can be represented as $\tau$; c) the apparent volume in which a drug is distributed, which can be represented as a volume of distribution $V_d$, where $V_d = D/C_0$; d) the amount of drug in a given volume of plasma, which can be represented as concentration $C_0$ or $C_{ss}$, where $C_0$ or $C_{ss} = D/Vd$; e) the half-life of a drug $t_{1/2}$, where $t_{1/2} = \ln(2)/k_e$; f) the rate at which a drug is removed from the body $k_e$, where $k_e = \ln(2)/t_{1/2} = CL/V_d$; g) the rate of infusion required to balance the equation $K_{in}$, where $K_{in} = C_{ss} \cdot CL$; h) the integral of the concentration-time curve after administration of a single dose, which can be represented as $AUC_{0-\infty}$, wherein $\int_0^\infty C\, dt$, or in steady-state, which can be represented as $AUC\tau_{ss}$, wherein $\int_t^{t+\tau} C\, dt$; i) the volume of plasma cleared of the drug per unit time, which can be represented as CL (clearance), wherein $CL = V_d \cdot k_e = D/AUC$; j) the systemically available fraction of a drug, which can be represented as f, where $$f = \frac{AUCpo \cdot Div}{AUCiv \cdot Dpo};$$

k) the peak plasma concentration of a drug after administration $C_{max}$; l) the time taken by a drug to reach $C_{max}$, $t_{max}$; m) the lowest concentration that a drug reaches before the next dose is administered $C_{min}$; and n) the peak trough fluctuation within one dosing interval at steady state, which can be represented as % PTF=100.

$$\frac{(C\max, ss - C\min, ss)}{Cav, ss} \text{ where } C_{av,ss} = \frac{AUC\tau, ss}{\tau}.$$

EXAMPLES

The following examples are provided to further illustrate the invention but not to limit its scope.

Example 1. Detecting ssDNA in Solution with Polycarbonate Immobilized Probes

This Example describes polycarbonate functionalized by a DNA probe and its utilizations for specific capture of ssDNA from solution.

Attachment of DNA probes to polycarbonate: The surface of polycarbonate was first nitrated and reduced to introduce amino groups which were used further to attach commercially available thiol/amino bifunctional linker (FIG. 1). DNA with 3' thiol modification was subsequently coupled to the linker tethered to the polycarbonate.

Figure 2:
FIG. 2 illustrates a polymer surface modified with DNA bearing 5'-Cy5 modification imaged with confocal microscope using Far Red filter. Area in the left portion of the image was modified.

Visualization of 5'-Cy5 modified DNA attached to polycarbonate: To visualize the DNA on the surface of the polycarbonate, DNA modified with one Cy5 at the 5' and thiol at the 3' was attached using chemistry described above. Single layer 5'Cy5-DNA was imaged with confocal microscopy (FIG. 2) showing successful functionalization of the surface. In vitro capture of ssDNA on polycarbonate modified with specific DNA probe: In order to test the ability of DNA probe attached to the polycarbonate to specifically capture (hybridize) ssDNA from the solution, polycarbonate disks were modified with DNA probe complementary to region of circular single stranded DNA (ssDNA, about 3.4 kb in size). Upon incubation of the modified disks with ssDNA solution, disks were thoroughly washed, hybridized ssDNA was released from the disks by denaturation at elevated temperature and quantified by quantitative PCR (qPCR). Amount of the DNA captured on the polycarbonate modified with specific DNA probe was expressed as ratio to the capture on polycarbonate modified with linker only—background control (FIG. 1).

Results obtained from the study are summarized in TABLE 1. The data show that the ssDNA target was successfully enriched on specific probe at all ssDNA concentrations tested (concentrations varying over 6 logs).

TABLE 1

TABLE 1. Capture efficiency as ratio of DNA recovery from disks with specific probe to recovery from disks modified with linker only.

| ssDNA sample conc. | Experiment/negative control DNA recovery |
| --- | --- |
| $1.66 \times 10^{-18}$ M (1.66 aM) | >4 |
| $1.66 \times 10^{-16}$ M (166 aM) | >3 |
| $1.66 \times 10^{-14}$ M (16.6 fM) | 11.4 |
| $1.66 \times 10^{-12}$ M (1.66 pM) | 5 |

Materials and methods used in the study are described in detail below.

Polycarbonate derivatization: polycarbonate was shaken in aqueous 30% HNO3 solution for 30 min at 65° C. and then washed extensively with water. Nitrated polycarbonate (step 1) was immersed into 10% solution of NaBH4 in water and shaken at room temperature overnight and finally washed extensively with water. Amino-modified polycarbonate (step 2) was immersed in 6.4 mM solution of Sulfo-GMBS (Pierce) in PBS pH 7.2 and shaken for 1.5 h at room temperature and finally washed extensively with water.

DNA thiol group deprotection: DNA was purchased from IDT with Thiol Modifier C3 S-S at the 3' end. To deprotect the thiol modification, 5 μL of 100 μM DNA solution in water was treated with 25 μL of 100 mM 2-mercaptoethanol in PBS pH 8.1 for 30 min at room temperature. To purify the deprotected DNA, 600 μL of PN buffer from Qiagen nucleotide removal kit was added to the reaction mixture followed by addition of isopropyl alcohol (250 μL). The solution was applied onto Qiagen nucleotide removal kit silica-column and washed according to kit's instructions followed by elution with 35 μL of PBS pH 7.2. DNA attachment to the polycarbonate: Solution of deprotected thiol modified DNA (step 4) was immediately applied onto polycarbonate modified with maleimide linker (step 3) and incubated at 37° C. in a humidified atmosphere for 45 min then washed extensively with water and dried in air.

Visualization of Cy5 modified DNA: 25 mer DNA modified with one Cy5 at the 5' end and thiol modification at the 3' end was attached to the surface of the polycarbonate using chemistry described above. After extensive washing with water and drying, polycarbonate was mounted onto microscope slide and imaged with confocal microscope using Far Red filter. The edge of DNA modified area on the surface was localized and imaged, clearly showing effect of modification with Cy5 labeled DNA monolayer.

Capture of ssDNA on polycarbonate functionalized with specific DNA probe: DNA probe with thiol modification at 3' (5'-CAAGTTTGCCTTTAGCGTCAGACTGTAT-TTTTTTT/ThioMC3/-3') (SEQ ID NO:1) was attached to polycarbonate disks using procedure described above (steps 1-4). Disks for negative control experiments were modified with linker only (steps 1-3). Disks were immersed in solution of circular ssDNA isolated from filamentous phage (for DNA concentrations see TABLE 1) in SSC buffer 3× (150 mM NaCl, 15 mM Sodium Citrate) and incubated for 10 min at 37° C. Disks were washed subsequently with three washing buffers. Washing buffer 1: 1×SSC+0.03% SDS; washing buffer 2: 0.2×SSC, washing buffer 3: 0.05×SSC. After washing, disk were immersed in minimal volume of sterile distilled water and heated at 90° C. for 2 minutes after which still warm water was removed from disks. ssDNA in aliquot of water solution was quantified using qPCR with primers specific for p3 gene of filamentous phage.

Example 2. Conjugation of DNA Probes to Stainless Steel Surfaces

Figure 3:
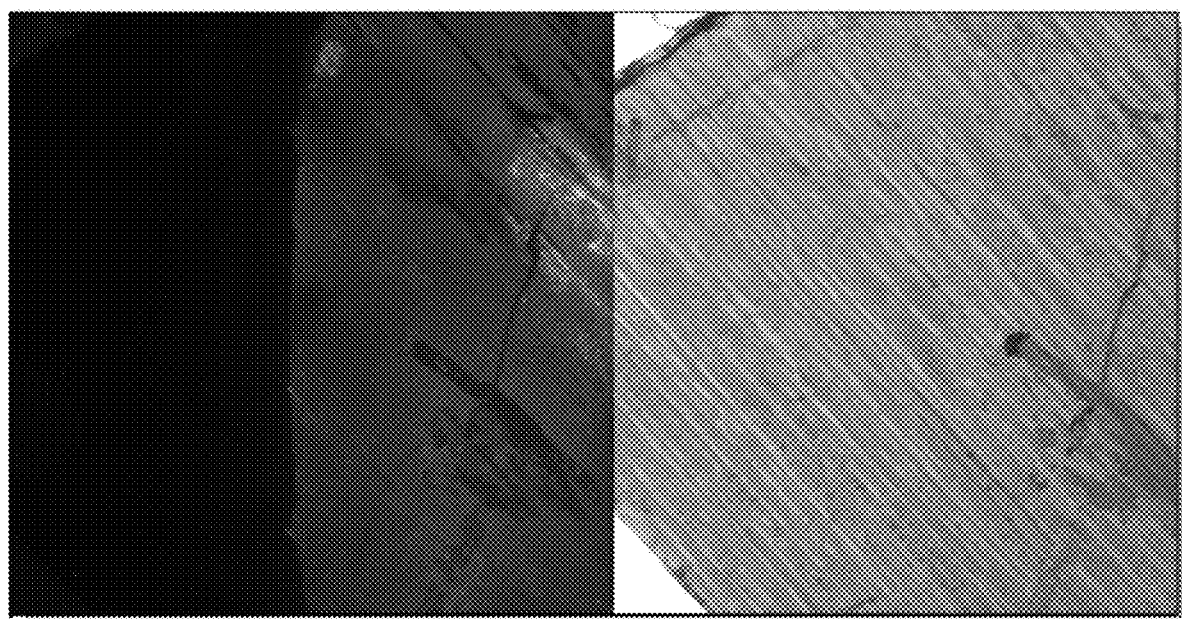
FIG. 3 illustrates a stainless steel surface modified with DNA containing fluorescent dUTP bases. Panel A. Fluorescent image of DNA on the steel surface. Panel B. Bright field image showing the surface of the stainless steel sample.

This Example describes attachment of DNA oligomer probes containing a 3' thiol modification to stainless steel surfaces coated in gold. Attachment of DNA probe to gold-coated stainless steel: Gold surfaces was readily modified by attaching thiol-derivatized single-stranded DNA. The sulfur atom of the thiolated DNA forms a covalent bond with gold. Visualization of DNA to gold-coated stainless steel: To visualize the DNA on the gold-coated surface of the stainless steel sample, a fill-in PCR reaction was performed to synthesize the complementary strand of the single-stranded DNA using fluorescently labeled dUTP. The resulting double-stranded oligomers contained multiple copies of Chromatide® Alexa Fluor® 488-5-dUTP, which fluoresces in the green channel, similar to fluorescein. Fluorescence microscopy demonstrates successful functionalization of the gold-coated stainless steel surface (FIG. 3).

Materials and methods used in the study are described in detail below.

DNA thiol group deprotection and conjugation to stainless steel: DNA was purchased from IDT with Thiol Modifier C3 S-S at the 3' end. To deprotect the thiol modification, 5 pL of 100 pM DNA solution in water was treated with 25 pL of 100 mM 2-mercaptoethanol in PBS pH 8.1 for 30 min at room temperature. To purify the deprotected DNA, 600 pL of PN buffer from Qiagen nucleotide removal kit was added to the reaction mixture followed by addition of isopropyl alcohol (300 pL). The solution was applied onto Qiagen nucleotide removal kit silica-column and washed according to kit's instructions followed by elution with 24 pL of TE buffer (10 mM Tris; 1 mM EDTA), pH 7.2.

A solution of deprotected thiol-modified DNA was immediately applied onto the gold surface of a piece of stainless steel (approximately 5 mm×2.5 mm). The solution was incubated at 37° C. in a humidified atmosphere for 16-20 hours and then washed extensively with water followed by air drying.

Fill-in reaction to amplify fluorescent signal: A 75 bp single-stranded DNA oligo with a thiol derivatization at the 3' end (5'-GCATGCATGCATGCATGCATGCATGCATG-CATGCATGCATGCGCCTGTGGGCGAC TAAAT-TCCGTTAAAGCCGGC/ThiolMC3/-3') (SEQ ID NO:2) was attached to the gold-coated surface of the sample of stainless steel. After washing and drying, the stainless steel sample was placed in a 0.5 mL tube. 48.5 pL of dH2O and 1.5 pL of a 10 pM primer complimentary to the 3' end of the thiol-derivatized DNA were then added. The mixture was incubated at 55° C. for 2 minutes to allow the primer to anneal to the single-stranded DNA. The mixture was then allowed to return to room temperature.

The fill in reaction was then performed using a Chromatide® Alexa Fluor® 488-5-dUTP purchased from Invitrogen. The following components were added to the mixture in step 3: 2 pL of 10 mM dNTP mix (dATP, dGTP, dCTP), 7.5 pL of 10× Klenow fragment buffer (New England Biolabs), 9.5 pL dH2O, 4 pL of 1 mM 488-5-dUTP and 2 pL of Klenow fragment (New England Biolabs). The reaction was incubated for 30 minutes at 37° C. The stainless steel sample was removed from the tub, washed extensively with water and allowed to air dry.

Visualization of Chromatide® Alexa Fluor® modified DNA: Once the sample of stainless steel had dried, it was mounted onto a microscope slide and imaged with a fluorescent microscope using the green filter. The edge of the DNA modified area on the stainless steel was localized and imaged, clearly demonstrating conjugation of the DNA to the gold-coated surface.

Figure 7:
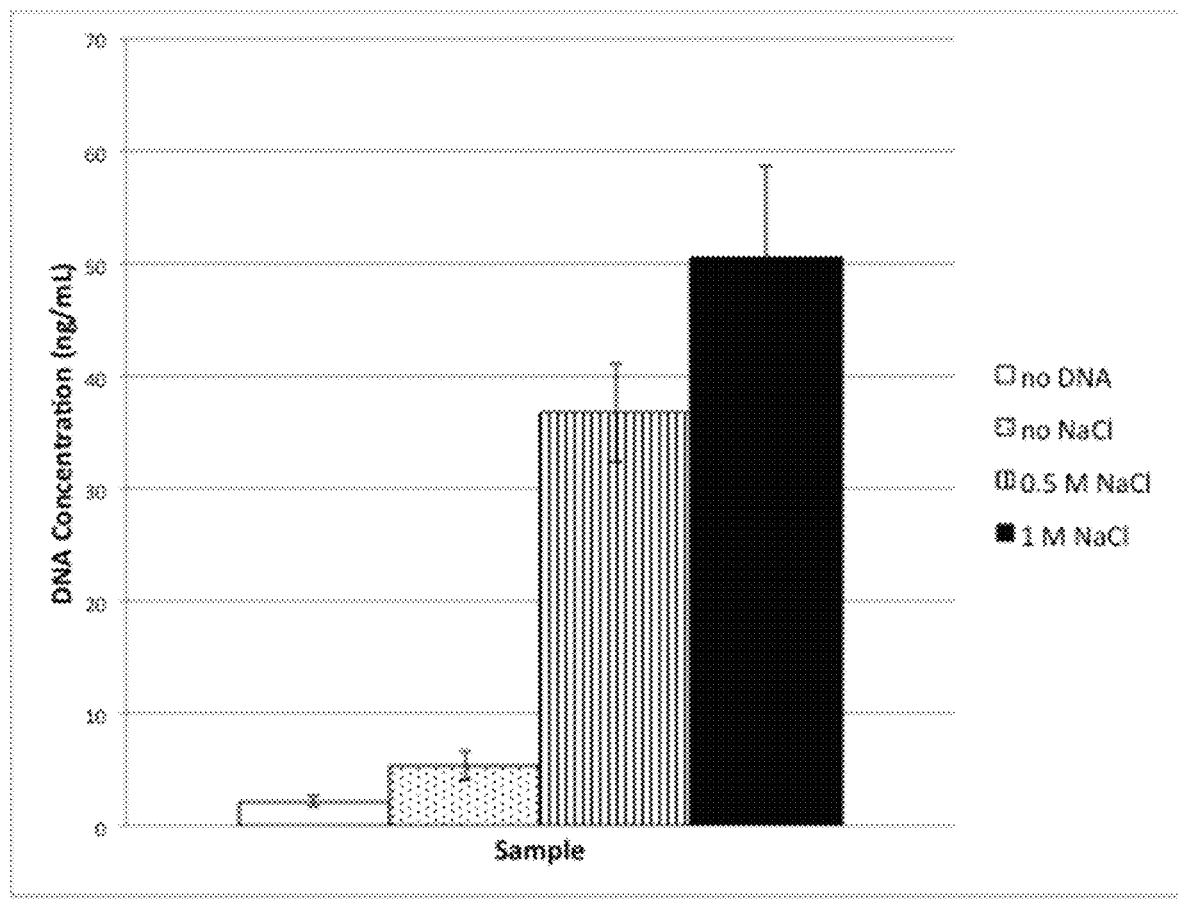
FIG. 7 exhibits the enhanced binding of oligonucleotides to the surface of metal microneedles arrays upon addition of NaCl to the coupling procedure.

Example 3. Enhanced Binding of Oligonucleotides to the Surface of Metal Microneedle Arrays To further facilitate the attachment of DNA oligomer probes containing a 3' thiol modification to stainless steel surfaces coated in gold, a NaCl titration was introduced. The protocol in EXAMPLE 2 described above was performed with the addition of increasing concentrations of NaCl. The amount of ssDNA coupled to the surface increased proportionally to the amount of NaCl added, and an approximately 10-fold increase was observed at the 1M NaCl concentration (FIG. 7). The quantitation of DNA bound to gold surface was determined using a Quanti-iT Green ssDNA Reagent Kit (Invitrogen).

Example 4. Methods of Diagnosis

Figure 5:
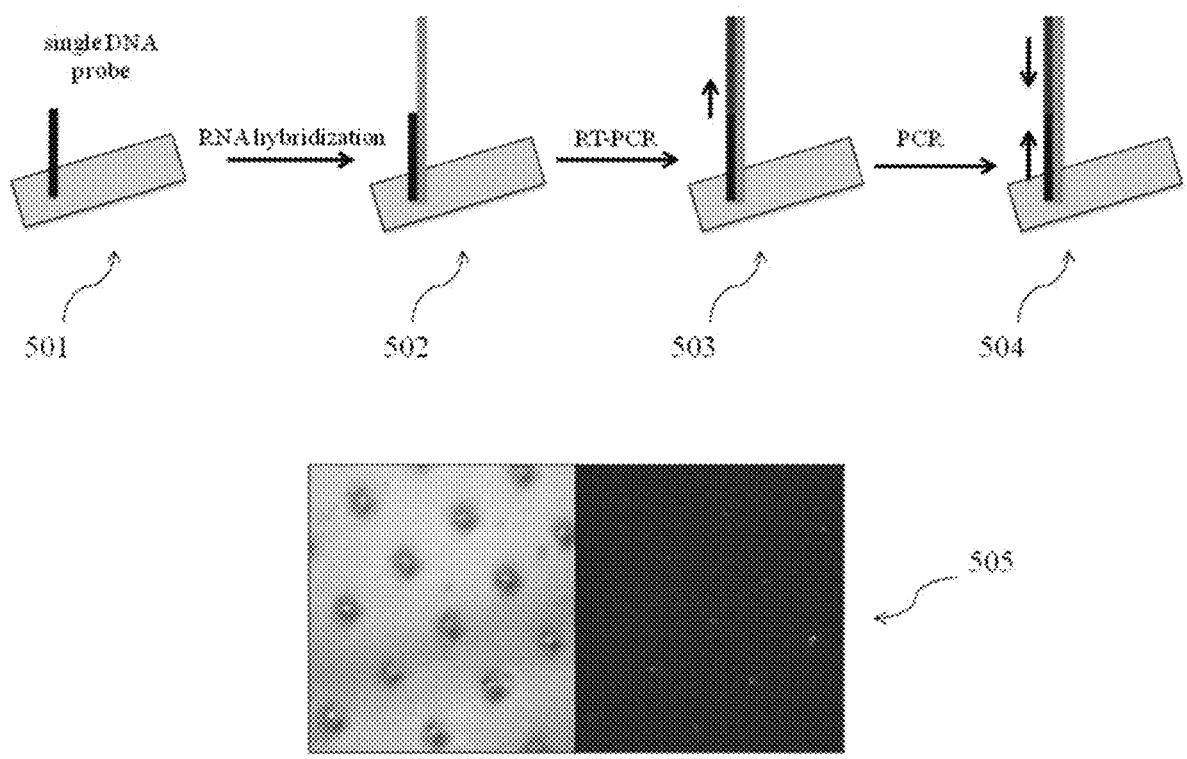
FIG. 5 illustrates a process whereby a DNA probe coupled to a gold surface hybridizes a biomarker.
Figure 6:
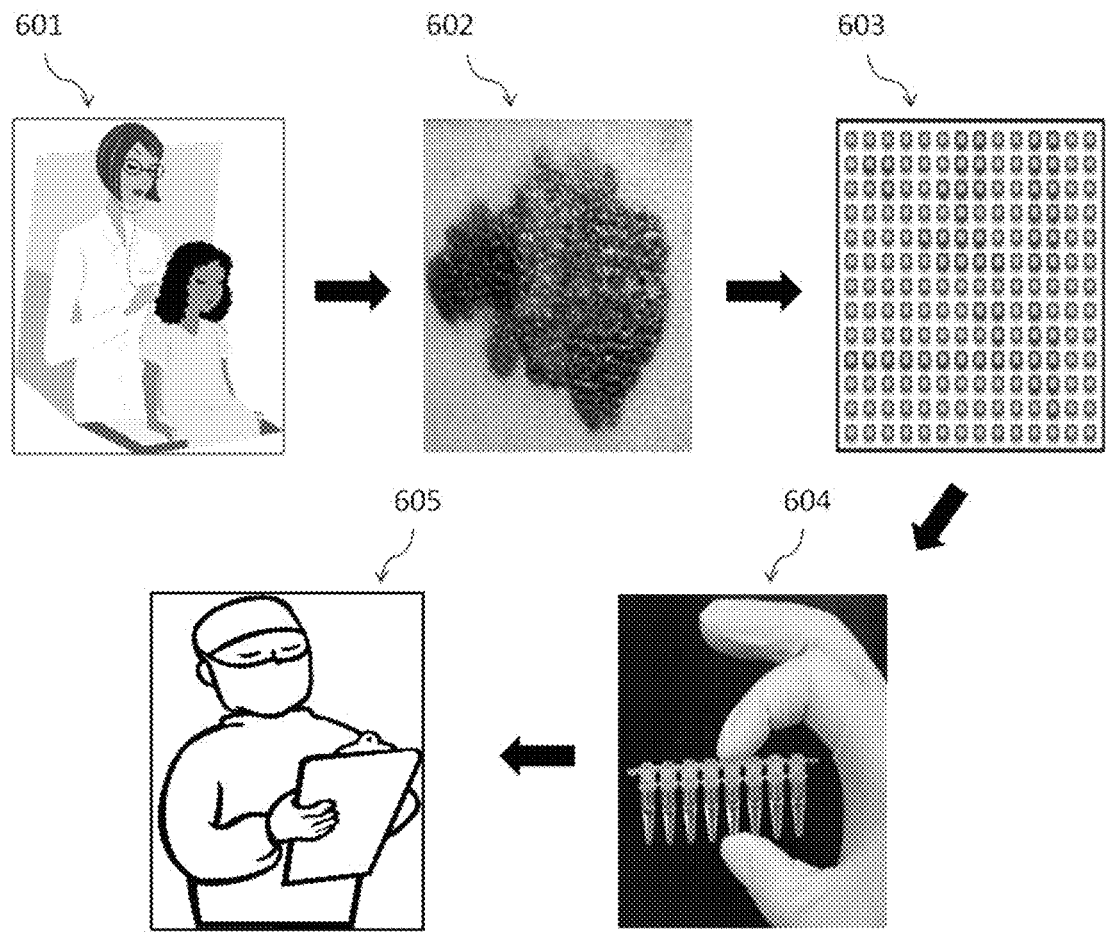
FIG. 6 illustrates a method of providing a treatment with a device of the disclosure.

Missing a melanoma diagnosis is a significant concern for dermatologists. The consequences of a missed diagnosis can be devastating for patients, costly for insurance companies, and damaging to physicians, therefore the early detection of melanoma is critical. Yet, the invasive nature of a standard biopsy procedure can deter a physician from pursuing a biopsy on a tissue that appears to be benign. FIGS. 5 and 6 illustrate the non-invasive diagnosis of melanoma with the devices and methods of the disclosure. 501-505 describes the surface of 603 in greater detail.

FIG. 5 illustrates a process whereby a DNA probe designed to detect a biomarker of melanoma hybridizes to the desired biomarker. 501 illustrates a single DNA probe attached to the gold surface of a microneedle. The DNA probe in 501 comprises a single nucleotide polymorphism that selectively hybridizes to an RNA associated with melanoma. The DNA probe in 501 was covalently linked to the gold surface in the microneedle as described in Example 2. 505 illustrates a bright-field and a fluorescent field image of the surface of a device of the invention, comprising a plurality of microneedles with covalently linked DNA probes. When the device touches the skin of the subject, the microneedles gently disrupt the membrane of the cells in the skin being contacted. This process exposes the probes on the microneedles to polynucleotide, peptide, and protein biomarkers within the cells. The probes on the microneedles can be allowed to hybridize 502 to the biomarkers for a specified period of time at physiological conditions in situ, e.x., the probes can be allowed to hybridize for about 30 minutes at physiological body temperature (about 37° C.). A reverse-transcriptase-PCR (RT-PCR) assay 503 can be utilized to convert the hybridized RNA into DNA. A standard PCR protocol 504 can be utilized to amplify the product of 503.

FIG. 6 illustrates an overview of the method of providing a treatment with a device of the invention. 601 illustrates a clinician conducting a visual inspection of a subject's skin. A clinician 601 can determine that a skin 602, or a portion of the skin, appears healthy or unhealthy. A clinician can touch the skin of the subject with a device of the invention, thereby contacting a probe for a biomarker to the skin of the subject in a non-invasive manner. 603 is a diagram of a surface of a device that was described in greater detail in FIG. 5. 604 illustrates a PCR assay that is performed to amplify the hybridized biomarker. 605 depicts a clinician returning the results of an analysis to a subject.

Example 5. In Vivo Testing of Modified Polymer Microneedle Arrays

This Example describes the in vivo detection of mouse actin using the modified polymer microneedle arrays described in this application. The polycarbonate microneedles were modified with a mouse actin ssDNA probe, and a sample of microneedles that had been coupled with a ssDNA probe was also coated with hyaluronidase. Mice (n=4; A/J, Swiss Webster) were treated with the ssDNA-modified polycarbonate microneedles. The microneedle arrays were applied to the shaved rear leg of mice using thumb pressure and held in place for approximately 10 seconds. mRNA that was bound to the arrays was then reverse transcribed into cDNA directly on the microneedle surface by inverting the array over a glass slide, sealing the space between the needle base and slide with oil, and placing the slide on a heat block for 30 minutes at 50° C. The reaction mixture was then transferred from the slide into a PCR tube and amplified using traditional PCR techniques. The cycling program went as follows: 94° C. for 1 min; 40 cycles of: 94° C. for 15 s, 55° C. for 30 s, 68° C. for 60 s; 68° C. for 5 min. The samples were visualized by gel imaging and quantitated using densitometry.

Significant increases in the amount of mRNA isolated from microneedles that contained probes was observed. The difference between samples that contained the ssDNA probe and unmodified microneedle arrays was ~2-3-fold while the difference between samples containing both ssDNA probes and hyaluronidase and unmodified arrays was ~8-fold. This shows that not only do the microneedles extract the target from the skin, but that interruption of the extracellular matrix can facilitate the extraction process, resulting in higher yields. A number of enzymes, including but not limited to serine proteases, thiol proteases, and MMPs, could be useful in this process. Further specific examples of enzymes include but are not limited to papain, hyaluronidase, streptokinase, streptodornase, trypsin, chymotrypsin, alpha-chymotrypsin, alpha-amlyase, DNase, collagenase, and sutilain.

Example 6. Isolation of Target mRNA from Homogenized Human Skin

This Example describes the isolation of target mRNA from homogenized human skin. Excess human skin including both cancerous and benign tissue was acquired from Scripps Clinic, which was excised during Mohs micrographic surgery. The skin was homogenized and the total RNA extracted using the following procedure. Skin was homogenized in RNAlater™ using a MP Biomedical Fast-Prep-24 and Lysing Matrix D beads (~30-40 mg tissue/tube) on a setting of 6.0 for 25 s. Total RNA was then isolated from this homogenate using a RNA extraction kit (Qiagen™) according to the manufacturer's instructions. DNA probes with sequences complimentary to human beta-actin were conjugated to gold coated stainless steel microneedles, placed into RNA solutions isolated from homogenized skin and incubated for periods of time at room temperature or at 37° C. Stainless steel strips were isolated from the solutions and the bound mRNA was reverse transcribed to cDNA, which was then amplified and analyzed using qRT-PCR. As a result, only the microneedles that were coupled to the beta-actin probe and subsequently amplified using the appropriate beta-actin probe yielded measureable amounts of target (FIG. 8). In this example, non-specific DNA sequences were conjugated to the microneedle surface; a BMP-4: Taqman probe was used against a non-actin target; and a Actb-human-1: beta-actin sequence was conjugated to the surface of a microneedle.

Example 7. Detection of mRNA from a Mouse Skin mRNA Library Using Microneedle Arrays In these experiments, target mRNA was isolated from a mouse skin mRNA library (Zyagen™). The total concentration of mRNA in the pool was 250 µg/mL. Gold-coated stainless steel microneedle arrays onto which probe ssDNA had been coupled were then added to the mRNA library (5 µL in 20 µL water) and incubated at 37° C. for approximately 10 minutes. Arrays were then washed gently and briefly allowed to air dry. cDNA synthesis then was performed by adding reverse transcriptase reaction mix (3 µL 10× reverse transcriptase buffer, 6 µL 25 mM $MgCl_2$, 3 µL 0.1 M DTT, 1.5 µL RNase OUT™, 13 µL DEPC water, 2 µL 10 mM dNTP mix) to tubes containing microneedle arrays and incubating at 42° C. for 2 minutes, followed by the addition of 1.5 µL of SuperScriptII™ reverse transcriptase. The reactions were cycled through the following program: 42° C. for 50 min, 70° C. for 15 min, and then on ice for approximately 15 min. RNase H was then added to each reaction (1.5 µL) and the reactions were incubated at 37° C. for 20 min. This was then followed by TaqMan™ PCR amplification using 20× TaqMan™ assay primer (1.5 µL), and 2× TaqMan™ gene expression mix (15 µL). Reactions had a total volume of 30 µL. After four cycles, 5 µL of the solution was removed and used as the template for TaqMan™ qRT-PCR (40 cycles) performed as per the manufacturer's instructions.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each was specifically and individually indicated to be incorporated by reference.

What is claimed is:

1. A device for extracting one or more mRNA biomarkers from an in situ tissue or a biopsied tissue of a subject, the device comprising two or more polymeric microneedles covalently attached to one or more nucleic acid probes specific for the one or more mRNA biomarkers, wherein a center-to-center distance between least two adjacent microneedles of the two or more polymeric microneedles is greater than 400 µm.

2. The device of claim 1, wherein the one or more nucleic acid probes specific for the one or more mRNA biomarkers comprise at least 50 nucleic acid probes specific for the one or more mRNA biomarkers.

3. The device of claim 2, wherein the at least 50 nucleic acid probes specific for the one or more mRNA biomarkers are covalently attached to at least one of the two or more polymeric microneedles.

4. The device of claim 1, wherein the device comprises one or more nucleic acid probes specific for a plurality of different mRNA biomarkers.

5. The device of claim 1, wherein the device comprises two or more polymeric microneedles attached to two or more nucleic acid probes, wherein the two or more nucleic acid probes comprise a same sequence.

6. The device of claim 1, wherein the one or more nucleic acid probes specific for the one or more mRNA biomarkers are polynucleotides complementary to the mRNA biomarkers.

7. The device of claim 6, wherein the two or more polymeric microneedles are polycarbonate, and the one or more nucleic acid probes are attached to the two or more polymeric microneedles via thiol/amino bifunctional linkers.

8. The device of claim 1, wherein the one or more nucleic acid probes are attached to the two or more polymeric microneedles via linkers.

9. The device of claim 8, wherein the linkers comprise a bifunctional linker.

10. The device of claim 8, wherein the linkers comprise a thiol/amino bifunctional linker.

11. The device of claim 8, wherein the linkers comprise a thiol linker.

12. The device of claim 8, wherein the linkers comprise a maleimide linker.

13. The device of claim 1, wherein the two or more polymeric microneedles are attached to a substrate.

14. The device of claim 1, wherein the one or more nucleic acid probes are not fluorescently labeled.

15. The device of claim 1, wherein the one or more nucleic acids probes comprise DNA.

16. The device of claim 1, wherein the one or more mRNA biomarkers comprise an mRNA associated with a skin condition.

17. The device of claim 16, wherein the one or more mRNA biomarkers comprise an mRNA associated with a skin condition selected from the group consisting of melanoma, non-melanocyte skin cancer, autoimmune disease, psoriasis, infection, and a combination thereof.

18. The device of claim 16, wherein the one or more mRNA biomarkers comprise an mRNA associated with melanoma.

19. The device of claim 16, wherein the one or more mRNA biomarkers comprise an mRNA associated with psoriasis.

20. The device of claim 1, wherein the two or more polymeric microneedles comprise at least 25 microneedles.

21. The device of claim 1, wherein the two or more polymeric microneedles comprise at least 50 microneedles.

22. A method for extracting and detecting one or more mRNA biomarkers from an in situ tissue or biological sample of a subject, comprising (a) providing a device for extracting one or more mRNA biomarkers from an in situ tissue or a biopsied tissue of a subject, the device comprising one or more polymeric microneedles covalently attached to one or more nucleic acid probes specific for the one or more mRNA biomarkers; (b) contacting the one or more polymeric microneedles of the device with the in situ tissue or biological sample of the subject; (c) extracting one or more mRNA biomarkers that are bound to the one or more nucleic acid probes; and (d) detecting the one or more mRNA biomarkers by sequencing.

23. The method of claim 22, wherein the device comprises one or more nucleic acid probes specific for a plurality of different mRNA biomarkers.

24. The method of claim 22, wherein the device comprises two or more polymeric microneedles and at least one of the two or more polymeric microneedles is attached to two or more nucleic acid probes, wherein the two or more nucleic acid probes comprise a same sequence.

25. The method of claim 22, wherein the one or more polymeric microneedles are formed on a substrate.

26. The method of claim 22, wherein the in situ tissue is the subject's bloodstream, and the one or more polymeric microneedles are contacted with the subject's bloodstream by piercing skin of the subject.

27. The method of claim 22, wherein the one or more mRNA biomarkers comprise an mRNA associated with a skin condition.

28. The method of claim 27, wherein the skin condition is melanoma, non-melanocyte skin cancer, autoimmune disease, psoriasis, infection, or a combination thereof.

29. The method of claim 28, wherein the skin condition is melanoma.

30. The method of claim 28, wherein the skin condition is psoriasis.

31. The method of claim 30, wherein the detecting the one or more mRNA biomarkers by sequencing comprises detecting one or more mRNA biomarkers released by the disruption of the cell membranes.

32. The method of claim 22, wherein the contacting the one or more polymeric microneedles of the device with the in situ tissue or biological sample of the subject disrupts cell membranes.

33. The method of claim 22, wherein the contacting the one or more polymeric microneedles of the device with the in situ tissue of the subject causes disruption of cell membranes.

34. The method of claim 22, wherein the in situ tissue or biological sample of the subject comprises skin.

35. The method of claim 22, wherein the contacting the one or more polymeric microneedles of the device with the in situ tissue or the biological sample of the subject comprises contacting the one or more polymeric microneedles of the device with the in situ tissue of the subject.

36. The method of claim 22, wherein the in situ tissue or biological sample of the subject comprises ocular tissue, retinal tissue, tumor tissue, or tissue biopsy.

37. The method of claim 22, wherein the contacting the one or more polymeric microneedles of the device with the in situ tissue or biological sample of the subject is conducted by manual pressure.

38. A device for extracting one or more cellular mRNA biomarkers from an in situ tissue or a biopsied tissue of a subject, comprising two or more polymeric microneedles covalently attached to one or more nucleic acid probes specific for the one or more cellular mRNA biomarkers.

* * * * *

SEQUENCE LISTING

```
<160> NUMBER OF SEQ ID NOS: 2

<210> SEQ ID NO 1
<211> LENGTH: 35
<212> TYPE: DNA
<213> ORGANISM: Artificial Sequence
<220> FEATURE:
<223> OTHER INFORMATION: Description of Artificial Sequence: Synthetic
      probe
<220> FEATURE:
<223> OTHER INFORMATION: 3' ThioMC3

<400> SEQUENCE: 1
caagtttgcc tttagcgtca gactgtattt ttttt                                35

<210> SEQ ID NO 2
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' ThiolMC3
```

-continued

```
<400> SEQUENCE: 2
gcatgcatgc atgcatgcat gcatgcatgc atgcatgcat gcgcctgtgg gcgactaaat        60
tccgttaaag ccggc                                                         75
```